(12) United States Patent
McCabe et al.

(10) Patent No.: US 10,254,443 B2
(45) Date of Patent: Apr. 9, 2019

(54) BIOMEDICAL DEVICES CONTAINING INTERNAL WETTING AGENTS

(71) Applicant: Johnson & Johnson Vision Care, Inc., Jacksonville, FL (US)

(72) Inventors: Kevin P. McCabe, St. Augustine, FL (US); Frank F. Molock, Jr., Birmingham (GB); Gregory A. Hill, Pleasant Valley, NY (US); Azaam Alli, Jacksonville, FL (US); Robert B. Steffen, Naples, FL (US); Douglas G. Vanderlaan, Jacksonville, FL (US); James D. Ford, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/917,924

(22) Filed: Mar. 12, 2018

(65) Prior Publication Data

US 2018/0203161 A1    Jul. 19, 2018

Related U.S. Application Data

(60) Continuation of application No. 14/570,475, filed on Jun. 25, 2015, now Pat. No. 9,958,577, which is a continuation of application No. 14/521,492, filed on Oct. 23, 2014, now Pat. No. 9,097,914, which is a continuation of application No. 13/848,945, filed on Mar. 22, 2013, now Pat. No. 8,895,687, which is a division of application No. 13/430,839, filed on Mar. 27, 2012, now Pat. No. 8,431,669, which is a division of application No. 12/630,219, filed on Dec. 3, 2009, now Pat. No. 8,168,720, which is a division of application No. 10/938,361, filed on Sep. 10, 2004, now Pat. No. 7,666,921, which is a division of application No. 10/236,538, filed on Sep. 6, 2002, now Pat. No. 6,822,016.

(60) Provisional application No. 60/318,536, filed on Sep. 10, 2001.

(51) Int. Cl.

| G02B 1/04 | (2006.01) |
| A61L 27/26 | (2006.01) |
| G02C 7/02 | (2006.01) |
| C08F 291/00 | (2006.01) |
| A61L 27/18 | (2006.01) |
| A61L 27/52 | (2006.01) |
| C08F 251/00 | (2006.01) |
| C08L 83/04 | (2006.01) |
| C08F 265/04 | (2006.01) |
| C08F 271/00 | (2006.01) |
| C08F 271/02 | (2006.01) |
| C08F 283/06 | (2006.01) |
| C08F 283/12 | (2006.01) |
| C08F 290/06 | (2006.01) |

(52) U.S. Cl.
CPC .............. *G02B 1/043* (2013.01); *A61L 27/18* (2013.01); *A61L 27/26* (2013.01); *A61L 27/52* (2013.01); *C08F 251/00* (2013.01); *C08F 265/04* (2013.01); *C08F 271/00* (2013.01); *C08F 271/02* (2013.01); *C08F 283/06* (2013.01); *C08F 283/12* (2013.01); *C08F 290/06* (2013.01); *C08F 291/00* (2013.01); *G02C 7/022* (2013.01)

(58) Field of Classification Search
None
See application file for complete search history.

(56) References Cited

U.S. PATENT DOCUMENTS

| 3,408,429 A | 10/1968 | Wichterle |
| 3,660,545 A | 5/1972 | Wichterle |
| 3,808,178 A | 4/1974 | Gaylord |
| 3,929,741 A | 12/1975 | Laskey |
| 3,966,847 A | 6/1976 | Seiderman |
| 4,113,224 A | 9/1978 | Clark et al. |
| 4,120,570 A | 10/1978 | Gaylord |
| 4,123,407 A | 10/1978 | Gordon |
| 4,123,408 A | 10/1978 | Gordon |
| 4,136,250 A | 1/1979 | Mueller et al. |
| 4,139,513 A | 2/1979 | Tanaka et al. |
| 4,139,548 A | 2/1979 | Tanaka et al. |
| 4,139,692 A | 2/1979 | Tanaka et al. |
| 4,153,641 A | 5/1979 | Deichert et al. |
| 4,190,277 A | 2/1980 | England |
| 4,197,266 A | 4/1980 | Clark et al. |
| 4,235,985 A | 11/1980 | Tanaka et al. |
| 4,259,467 A | 3/1981 | Keogh et al. |
| 4,260,725 A | 4/1981 | Keogh et al. |
| 4,261,875 A | 4/1981 | LeBoeuf |

(Continued)

FOREIGN PATENT DOCUMENTS

| CN | 1684723 A | 10/2005 |
| CN | 1780883 A | 5/2006 |

(Continued)

OTHER PUBLICATIONS

Barton, Allan F. M., Tables 13-15, CRC Handbook of Solubility Parameters and Other Cohesion Parameters, 1983, pp. 85-87, 1, CRC Press, Inc., Boca Raton, Florida.

(Continued)

*Primary Examiner* — John J Figueroa

(74) *Attorney, Agent, or Firm* — Raef M. Shaltout

(57) ABSTRACT

This invention includes a wettable biomedical device containing a high molecular weight hydrophilic polymer and a hydroxyl-functionalized silicone-containing monomer.

47 Claims, No Drawings

(56) References Cited

U.S. PATENT DOCUMENTS

| | | |
|---|---|---|
| 4,277,595 A | 7/1981 | Deichert et al. |
| 4,294,974 A | 10/1981 | LeBoeuf |
| 4,303,772 A | 12/1981 | Novicky |
| 4,487,905 A | 12/1984 | Mitchell |
| 4,495,313 A | 1/1985 | Larsen |
| 4,649,184 A | 3/1987 | Yoshikawa et al. |
| 4,659,777 A | 4/1987 | Riffle et al. |
| 4,680,336 A | 7/1987 | Larsen et al. |
| 4,711,943 A | 12/1987 | Harvey, III |
| 4,740,533 A | 4/1988 | Su et al. |
| 4,771,089 A | 9/1988 | Ofstead |
| 4,810,764 A | 3/1989 | Friends et al. |
| 4,889,664 A | 12/1989 | Kindt-Larsen et al. |
| 4,910,277 A | 3/1990 | Bambury et al. |
| 4,954,587 A | 9/1990 | Mueller |
| 5,006,622 A | 4/1991 | Kunzler et al. |
| 5,010,141 A | 4/1991 | Mueller |
| 5,034,461 A | 7/1991 | Lai et al. |
| 5,039,459 A | 8/1991 | Kindt-Larsen et al. |
| 5,070,215 A | 12/1991 | Bambury et al. |
| 5,152,788 A | 10/1992 | Isaacson et al. |
| 5,219,965 A | 6/1993 | Valint, Jr. et al. |
| 5,244,981 A | 9/1993 | Seidner et al. |
| 5,256,751 A | 10/1993 | Vanderlaan |
| 5,258,490 A | 11/1993 | Chang |
| 5,260,000 A | 11/1993 | Nandu et al. |
| 5,274,008 A | 12/1993 | Lai |
| 5,304,584 A | 4/1994 | Nunez et al. |
| 5,311,223 A | 5/1994 | Vanderlaan |
| 5,314,960 A | 5/1994 | Spinelli et al. |
| 5,314,961 A | 5/1994 | Anton et al. |
| 5,320,843 A | 6/1994 | Raheja et al. |
| 5,321,108 A | 6/1994 | Kunzler et al. |
| 5,331,067 A | 7/1994 | Seidner et al. |
| 5,334,681 A | 8/1994 | Mueller et al. |
| 5,352,714 A | 10/1994 | Lai et al. |
| 5,357,013 A | 10/1994 | Bambury et al. |
| 5,358,995 A | 10/1994 | Lai et al. |
| 5,364,918 A | 11/1994 | Valint, Jr. et al. |
| 5,371,147 A | 12/1994 | Spinelli et al. |
| 5,387,632 A | 2/1995 | Lai et al. |
| 5,387,662 A | 2/1995 | Kunzler et al. |
| 5,426,158 A | 6/1995 | Mueller et al. |
| 5,451,617 A | 9/1995 | Lai et al. |
| 5,484,863 A | 1/1996 | Molock et al. |
| 5,486,579 A | 1/1996 | Lai et al. |
| 5,525,691 A | 6/1996 | Valint, Jr. et al. |
| 5,534,605 A | 7/1996 | Bambury et al. |
| 5,539,016 A | 7/1996 | Kunzler et al. |
| 5,565,539 A | 10/1996 | Nunez et al. |
| 5,589,563 A | 12/1996 | Ward et al. |
| 5,690,953 A | 11/1997 | Molock et al. |
| 5,710,302 A | 1/1998 | Kunzler et al. |
| 5,726,733 A | 3/1998 | Lai et al. |
| 5,760,100 A | 6/1998 | Nicolson et al. |
| 5,776,611 A | 7/1998 | Elton et al. |
| 5,776,999 A | 7/1998 | Nicolson et al. |
| 5,789,461 A | 8/1998 | Nicolson et al. |
| 5,849,811 A | 12/1998 | Nicolson et al. |
| 5,851,585 A | 12/1998 | Gupta et al. |
| 5,944,853 A | 8/1999 | Molock et al. |
| 5,959,117 A | 9/1999 | Ozark et al. |
| 5,962,548 A | 10/1999 | Vanderlaan et al. |
| 5,965,631 A | 10/1999 | Nicolson et al. |
| 5,981,675 A | 11/1999 | Valint, Jr. et al. |
| 5,994,488 A | 11/1999 | Yokota et al. |
| 5,998,498 A | 12/1999 | Vanderlaan et al. |
| 6,013,711 A | 1/2000 | Lewis et al. |
| 6,020,445 A | 2/2000 | Vanderlaan et al. |
| 6,071,112 A | 6/2000 | Calvin |
| 6,087,415 A | 7/2000 | Vanderlaan et al. |
| 6,099,852 A | 8/2000 | Jen |
| 6,218,503 B1 | 4/2001 | Lai et al. |
| 6,242,041 B1 | 6/2001 | Katoot |
| 6,367,929 B1 | 4/2002 | Maiden et al. |
| 6,440,571 B1 | 8/2002 | Valint, Jr. et al. |
| 6,649,722 B2 | 11/2003 | Rosenzweig et al. |
| 6,818,719 B2 | 11/2004 | Fujisawa et al. |
| 6,822,016 B2 | 11/2004 | McCabe et al. |
| 6,867,245 B2 | 3/2005 | Iwata et al. |
| 7,052,131 B2 | 5/2006 | McCabe et al. |
| 7,071,274 B2 | 7/2006 | Fujisawa et al. |
| 7,112,641 B2 | 9/2006 | Fujisawa et al. |
| 7,317,117 B2 | 1/2008 | Nakamura et al. |
| 7,329,694 B2 | 2/2008 | Nakamura et al. |
| 7,649,058 B2 | 1/2010 | McCabe et al. |
| 7,666,921 B2 | 2/2010 | McCabe et al. |
| 7,691,916 B2 | 4/2010 | McCabe et al. |
| 2002/0099112 A1* | 7/2002 | Turner .................. B29C 33/42 523/107 |
| 2002/0107324 A1 | 8/2002 | Vanderlaan et al. |
| 2003/0052424 A1 | 3/2003 | Turner et al. |
| 2003/0109637 A1 | 6/2003 | Kunzler et al. |
| 2004/0002556 A1 | 1/2004 | Molock et al. |
| 2004/0054106 A1 | 3/2004 | Ito et al. |
| 2004/0198916 A1 | 10/2004 | Nakamura et al. |
| 2004/0198938 A1 | 10/2004 | Nakamura et al. |
| 2004/0209973 A1* | 10/2004 | Steffen ................ C08F 230/08 523/107 |
| 2005/0154080 A1 | 7/2005 | McCabe et al. |
| 2006/0007391 A1 | 1/2006 | McCabe et al. |
| 2006/0012750 A1 | 1/2006 | Nakamura et al. |
| 2006/0229423 A1 | 10/2006 | Parakka et al. |
| 2011/0237766 A1 | 9/2011 | Maggio et al. |

FOREIGN PATENT DOCUMENTS

| | | |
|---|---|---|
| EP | 0080539 B1 | 6/1983 |
| EP | 0094153 A2 | 11/1983 |
| EP | 0131468 B1 | 1/1985 |
| EP | 0124017 B1 | 7/1989 |
| EP | 0420403 B1 | 10/1993 |
| EP | 0560916 B1 | 2/1997 |
| EP | 0643083 B1 | 5/1997 |
| EP | 0396364 B1 | 6/1997 |
| EP | 0989418 A2 | 3/2000 |
| EP | 0908744 B1 | 12/2002 |
| EP | 1019416 B1 | 1/2003 |
| EP | 0735092 B1 | 9/2003 |
| EP | 0985520 B1 | 1/2004 |
| EP | 0940693 B1 | 6/2005 |
| JP | 54055455 | 5/1979 |
| JP | 11228644 | 8/1999 |
| JP | 11316358 | 11/1999 |
| JP | 2000137195 | 5/2000 |
| JP | 2006519907 | 8/2006 |
| TW | 200500195 | 1/2005 |
| TW | 229683 B | 3/2005 |
| WO | 9104283 A1 | 4/1991 |
| WO | 1991004288 A1 | 4/1991 |
| WO | 1992018548 A1 | 10/1992 |
| WO | 9309154 A1 | 5/1993 |
| WO | 1995020476 A1 | 8/1995 |
| WO | 9631792 A1 | 10/1996 |
| WO | 9720852 A1 | 6/1997 |
| WO | 1998007054 A1 | 2/1998 |
| WO | 2000002937 A1 | 1/2000 |
| WO | 2000035365 A1 | 6/2000 |
| WO | 2001027174 A1 | 4/2001 |
| WO | 2001030558 A1 | 5/2001 |
| WO | 2001070824 A2 | 9/2001 |
| WO | 2001070837 A1 | 9/2001 |
| WO | 2002016974 A2 | 2/2002 |
| WO | 2002020631 | 3/2002 |
| WO | 2002031007 A1 | 4/2002 |
| WO | 2002081485 A1 | 10/2002 |
| WO | 2002081532 A1 | 10/2002 |
| WO | 2003021336 A1 | 3/2003 |
| WO | 2003021337 A1 | 3/2003 |
| WO | 2003022321 A2 | 3/2003 |
| WO | 2003022322 A2 | 3/2003 |
| WO | 2003027123 A1 | 4/2003 |
| WO | 2003042222 A1 | 5/2003 |
| WO | 2004081105 A2 | 9/2004 |

(56) References Cited

FOREIGN PATENT DOCUMENTS

| WO | 2005005517 A2 | 1/2005 |
|---|---|---|
| WO | 2006002894 A1 | 1/2006 |
| WO | 2006039466 A1 | 4/2006 |

OTHER PUBLICATIONS

Crivello, et al, Photoinitiators for Free Radical Cationic & Anionic Photopolymerisation, 2nd Edition, vol. III, pp. 275-298, John Wiley and Sons, New York, 1998.
Encyclopedia of Polymer Science and Engineering, N-Vinyl Amide Polymers, Second edition, vol. 17, pp. 198-257, John Wiley & Sons Inc. and reported in K-values.
Extended European Search Report for EP 16161217 dated Jul. 13, 2016.
Kunzler, "Silicone Hydrogels for Contact Lens Application", Trends in Polymer Science, Feb. 1996, pp. 52-59, vol. 4, No, 2, Elsevier Trends Journals, Cambridge, UK.
Lander et al, A Systematic Comparison of Contact Angle Methods, Langmuir, 1993, vol. 9, pp. 22237-22239.
Proceedings of the American Chemical Society Division of Polymeric Materials: Science and Engineering, Apr. 13-17, 1997, p. 42.
Veys, et al, "Assessment of the Tear Film", Essential Contact Lens Practice, Jan. 1, 2008, pp. 1-12. Retrieved from the Internet. URL:http://www.thevisioncareinstitute.co.uk/site/dault/files/private/uk/pdf/ECLP Chapter 4.PDF.

* cited by examiner

BIOMEDICAL DEVICES CONTAINING INTERNAL WETTING AGENTS

RELATED PATENT APPLICATIONS

This application is a continuation of U.S. patent application Ser. No. 14/750,475, filed on Jun. 25, 2015; which is a continuation of U.S. patent application Ser. No. 14/521,492, filed on Oct. 23, 2014, now U.S. Pat. No. 9,097,914, issued on Aug. 4, 2015; which is a continuation of U.S. patent application Ser. No. 13/848,945, filed on Mar. 22, 2013, now U.S. Pat. No. 8,895,687, issued on Nov. 25, 2014; which is a division of U.S. patent application Ser. No. 13/430,839 filed on Mar. 27, 2012, now U.S. Pat. No. 8,431,669, issued on Apr. 30, 2013; which is a division of U.S. patent application Ser. No. 12/630,219 filed on Dec. 3, 2009, now U.S. Pat. No. 8,168,720, issued on May 1, 2012; which is a division of U.S. patent application Ser. No. 10/938,361 filed on Sep. 10, 2004, now U.S. Pat. No. 7,666,921, issued on Feb. 23, 2010; which is a division of U.S. patent application Ser. No. 10/236,538 filed on Sep. 6, 2002, now U.S. Pat. No. 6,822,016, issued on Nov. 23, 2004; which claimed priority of provisional application, U.S. Ser. No. 60/318,536 filed on Sep. 10, 2001, now expired.

FIELD OF THE INVENTION

This invention relates to silicone hydrogels that contain internal wetting agents, as well as methods for their production and use.

BACKGROUND OF THE INVENTION

Contact lenses have been used commercially to improve vision since at least the 1950s. The first contact lenses were made of hard materials and as such were somewhat uncomfortable to users. Modern lenses have been developed that are made of softer materials, typically hydrogels and particularly silicone hydrogels. Silicone hydrogels are water-swollen polymer networks that have high oxygen permeability and surfaces that are more hydrophobic than hydrophilic. These lenses provide a good level of comfort to many lens wearers, but there are some users who experience discomfort and excessive ocular deposits leading to reduced visual acuity when using these lenses. This discomfort and deposits has been attributed to the hydrophobic character of the surfaces of lenses and the interaction of those surfaces with the protein, lipids and mucin and the hydrophilic surface of the eye.

Others have tried to alleviate this problem by coating the surface of silicone hydrogel contact lenses with hydrophilic coatings, such as plasma coatings Uncoated lenses having low incidences of surface deposits are not disclosed.

Incorporating internal hydrophilic agents (or wetting agents) into a macromer containing reaction mixture has been disclosed. However, not all silicone containing macromers display compatibility with hydrophilic polymers. Modifying the surface of a polymeric article by adding polymerizable surfactants to a monomer mix used to form the article has also been disclosed. However, lasting in vivo improvements in wettability and reductions in surface deposits are not likely.

Polyvinylpyrrolidone (PVP) or poly-2-ethyl-2-oxazoline have been added to a hydrogel composition to form an interpenetrating network which shows a low degree of surface friction, a low dehydration rate and a high degree of biodeposit resistance. However, the hydrogel formulations disclosed are conventional hydrogels and there is no disclosure on how to incorporate hydrophobic components, such as siloxane monomers, without losing monomer compatibility.

While it may be possible to incorporate high molecular weight polymers as internal wetting agents into silicone hydrogel lenses, such polymers are difficult to solubilize in reaction mixtures which contain silicones. In order to solubilize these wetting agents, silicone macromers or other prepolymers must be used. These silicone macromers or prepolymers must be prepared in a separate step and then subsequently mixed with the remaining ingredients of the silicone hydrogel formulation. This additional step (or steps) increases the cost and the time it takes to produce these lenses. Moreover, these approaches have failed to produce an ophthalmic device which is sufficiently wettable to allow its use as a contact lens without a coating.

Therefore it would be advantageous to find a lens formulation that does not require the use of silicone macromers or other prepolymers and is suitable for extended wear without a surface treatment.

SUMMARY OF THE INVENTION

The present invention relates to wettable silicone hydrogels formed from a reaction mixture comprising, consisting essentially of or consisting of at least one high molecular weight hydrophilic polymer and at least one hydroxyl-functionalized silicone-containing monomer.

The present invention further relates to biomedical devices formed from a reaction mixture comprising, consisting essentially of, or consisting of a high molecular weight hydrophilic polymer and an effective amount of an hydroxyl-functionalized silicone-containing monomer.

The present invention further relates to a method of preparing a biomedical device comprising, consisting essentially of or consisting of mixing a high molecular weight hydrophilic polymer and an effective amount of a hydroxyl-functionalized silicone-containing monomer to form a clear solution, and curing said solution.

The present invention yet further relates to a method comprising, consisting essentially of or consisting of the steps of (a) mixing a high molecular weight hydrophilic polymer and an effective amount of an hydroxyl-functionalized silicone-containing monomer and (b) curing the product of step (a) to form a biomedical device.

The present invention yet further relates to a method comprising, consisting essentially of or consisting of the steps of (a) mixing a high molecular weight hydrophilic polymer and an effective amount of a hydroxyl-functionalized silicone containing monomer and (b) curing the product of step (a) at or above a minimum gel time, to form a wettable biomedical device.

The present invention still further relates to a method for improving the wettability of an ophthalmic device formed from a reaction mixture comprising, consisting essentially of and consisting of adding at least one high molecular weight hydrophilic polymer and an effective amount of at least one compatibilizing monomer to said reaction mixture.

The present invention still further relates to a method for improving the wettability of an ophthalmic device formed from a reaction mixture comprising, consisting essentially of and consisting of adding at least one high molecular weight hydrophilic polymer and an effective amount of at least one hydroxyl-functionalized silicone containing monomer to said reaction mixture.

The present invention still further relates to a biomedical device formed from a reaction mixture comprising, consisting essentially of and consisting of at least one hydroxyl-functionalized silicone-containing monomer and an amount of high molecular weight hydrophilic polymer sufficient to provide said device, without a surface treatment, with an advancing contact angle of less than about 80°, less than about 70° or less than about 60°.

The present invention still further relates to an ophthalmic device formed from a reaction mixture comprising, consisting essentially of or consisting of at least one hydroxyl-functionalized silicone-containing monomer and an amount of high molecular weight hydrophilic polymer sufficient to provide said device, without a surface treatment, with a tear film break up time after about one day of wear of at least about 7 seconds or equal to or greater than tear film break up time for an ACUVUE® contact lens.

A device comprising a silicone hydrogel contact lens which is substantially free from surface deposition without surface modification

DETAILED DESCRIPTION OF THE INVENTION

It has been surprisingly found that biomedical devices, and particularly ophthalmic devices having exceptional in vivo or clinical wettability, without surface modification, may be made by including an effective amount of a high molecular weight hydrophilic polymer and an effective amount of a hydroxyl-functionalized silicone-containing monomer in a silicone hydrogel formulation. By exceptional wettability we mean a decrease in advancing dynamic contact angle of at least about 10% and preferably at least about 20% in some embodiments at least about 50% as compared to a similar formulation without any hydrophilic polymer. Prior to the present invention ophthalmic devices formed from silicone hydrogels either had to be surface modified to provide clinical wettability or be formed from at least one silicone containing macromer having hydroxyl functionality.

As used herein, a "biomedical device" is any article that is designed to be used while either in or on mammalian tissues or fluid, and preferably in or on human tissue or fluids. Examples of these devices include but are not limited to catheters, implants, stents, and ophthalmic devices such as intraocular lenses and contact lenses. The preferred biomedical devices are ophthalmic devices, particularly contact lenses, most particularly contact lenses made from silicone hydrogels.

As used herein, the terms "lens" and "ophthalmic device" refer to devices that reside in or on the eye. These devices can provide optical correction, wound care, drug delivery, diagnostic functionality, cosmetic enhancement or effect or a combination of these properties. The term lens includes but is not limited to soft contact lenses, hard contact lenses, intraocular lenses, overlay lenses, ocular inserts, and optical inserts.

As used herein the term "monomer" is a compound containing at least one polymerizable group and an average molecular weight of about less than 2000 Daltons, as measure via gel permeation chromatography refractive index detection. Thus, monomers include dimers and in some cases oligomers, including oligomers made from more than one monomeric unit.

As used herein, the phrase "without a surface treatment" means that the exterior surfaces of the devices of the present invention are not separately treated to improve the wettability of the device. Treatments which may be foregone because of the present invention include, plasma treatments, grafting, coating and the like. However, coatings which provide properties other than improved wettability, such as, but not limited to antimicrobial coatings may be applied to devices of the present invention.

Various molecular weight ranges are disclosed herein. For compounds having discrete molecular structures, the molecular weights reported herein are calculated based upon the molecular formula and reported in gm/mol. For polymers molecular weights (number average) are measured via gel permeation chromatography refractive index detection and reported in Daltons or are measured via kinematic viscosity measurements, as described in Encyclopedia of Polymer Science and Engineering, N-Vinyl Amide Polymers, Second edition, Vol. 17, pgs. 198-257, John Wiley & Sons Inc. and reported in K-values.

High Molecular Weight Hydrophilic Polymer

As used herein, "high molecular weight hydrophilic polymer" refers to substances having a weight average molecular weight of no less than about 100,000 Daltons, wherein said substances upon incorporation to silicone hydrogel formulations, increase the wettability of the cured silicone hydrogels. The preferred weight average molecular weight of these high molecular weight hydrophilic polymers is greater than about 150,000; more preferably between about 150,000 to about 2,000,000 Daltons, more preferably still between about 300,000 to about 1,800,000 Daltons, most preferably about 500,000 to about 1,500,000 Daltons.

Alternatively, the molecular weight of hydrophilic polymers of the invention can be also expressed by the K-value, based on kinematic viscosity measurements, as described in Encyclopedia of Polymer Science and Engineering, N-Vinyl Amide Polymers, Second edition, Vol. 17, pgs. 198-257, John Wiley & Sons Inc. When expressed in this manner, hydrophilic monomers having K-values of greater than about 46 and preferably between about 46 and about 150. The high molecular weight hydrophilic polymers are present in the formulations of these devices in an amount sufficient to provide contact lenses, which without surface modification remain substantially free from surface depositions during use. Typical use periods include at least about 8 hours, and preferably worn several days in a row, and more preferably for 24 hours or more without removal. Substantially free from surface deposition means that, when viewed with a slit lamp, at least about 70% and preferably at least about 80%, and more preferably about 90% of the lenses worn in the patient population display depositions rated as none or slight, over the wear period.

Suitable amounts of high molecular weight hydrophilic polymer include from about 1 to about 15 weight percent, more preferably about 3 to about 15 percent, most preferably about 5 to about 12 percent, all based upon the total of all reactive components.

Examples of high molecular weight hydrophilic polymers include but are not limited to polyamides, polylactones, polyimides, polylactams and functionalized polyamides, polylactones, polyimides, polylactams, such as DMA functionalized by copolymerizing DMA with a lesser molar amount of a hydroxyl-functional monomer such as HEMA, and then reacting the hydroxyl groups of the resulting copolymer with materials containing radical polymerizable groups, such as isocyanatoethylmethacrylate or methacryloyl chloride. Hydrophilic prepolymers made from DMA or n-vinyl pyrrolidone with glycidyl methacrylate may also be used. The glycidyl methacrylate ring can be opened to give a diol which may be used in conjunction with other hydrophilic prepolymer in a mixed system to increase the compatibility of the high molecular weight hydrophilic polymer, hydroxyl-functionalized silicone containing monomer and any other groups which impart compatibility. The preferred high molecular weight hydrophilic polymers are those that contain a cyclic moiety in their backbone, more preferably, a cyclic amide or cyclic imide. High molecular weight hydrophilic polymers include but are not limited to poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N—N-dimethylacrylamide, polyvinyl alcohol, polyacrylic acid, polyethylene oxide, poly 2 ethyl oxazoline, heparin polysaccharides, polysaccharides, mixtures and copolymers (including block or random, branched, multichain, comb-shaped or star shaped) thereof where poly-N-vinylpyrrolidone (PVP) is particularly preferred. Copolymers might also be used such as graft copolymers of PVP.

The high molecular weight hydrophilic polymers provide improved wettability, and particularly improved in vivo wettability to the medical devices of the present invention. Without being bound by any theory, it is believed that the high molecular weight hydrophilic polymers are hydrogen bond receivers which in aqueous environments, hydrogen bond to water, thus becoming effectively more hydrophilic. The absence of water facilitates the incorporation of the hydrophilic polymer in the reaction mixture. Aside from the specifically named high molecular weight hydrophilic polymers, it is expected that any high molecular weight polymer will be useful in this invention provided that when said polymer is added to a silicone hydrogel formulation, the hydrophilic polymer (a) does not substantially phase separate from the reaction mixture and (b) imparts wettability to the resulting cured polymer. In some embodiments it is preferred that the high molecular weight hydrophilic polymer be soluble in the diluent at processing temperatures. Manufacturing processes which use water or water soluble diluents may be preferred due to their simplicity and reduced cost. In these embodiments high molecular weight hydrophilic polymers which are water soluble at processing temperatures are preferred.

Hydroxyl-Functionalized Silicone Containing Monomer

As used herein a "hydroxyl-functionalized silicone containing monomer" is a compound containing at least one polymerizable group having an average molecular weight of about less than 5000 Daltons as measured via gel permeation chromatography, refractive index detection, and preferably less than about 3000 Daltons, which is capable of compatibilizing the silicone containing monomers included in the hydrogel formulation with the hydrophilic polymer. Hydroxyl functionality is very efficient at improving hydrophilic compatibility. Thus, in a preferred embodiment hydroxyl-functionalized silicone containing monomers of the present invention comprise at least one hydroxyl group and at least one "—Si—O—Si—" group. It is preferred that silicone and its attached oxygen account for more than about 10 weight percent of said hydroxyl-functionalized silicone containing monomer, more preferably more than about 20 weight percent.

The ratio of Si to OH in the hydroxyl-functionalized silicone containing monomer is also important to providing a hydroxyl functionalized silicone containing monomer which will provide the desired degree of compatibilization. If the ratio of hydrophobic portion to OH is too high, the hydroxyl-functionalized silicone monomer may be poor at compatibilizing the hydrophilic polymer, resulting in incompatible reaction mixtures. Accordingly, in some embodiments, the Si to OH ratio is less than about 15:1, and preferably between about 1:1 to about 10:1. In some embodiments primary alcohols have provided improved compatibility compared to secondary alcohols. Those of skill in the art will appreciate that the amount and selection of hydroxyl-functionalized silicone containing monomer will depend on how much hydrophilic polymer is needed to achieve the desired wettability and the degree to which the silicone containing monomer is incompatible with the hydrophilic polymer.

Examples of hydroxyl-functionalized silicone containing monomers include monomers of Formulae I and II

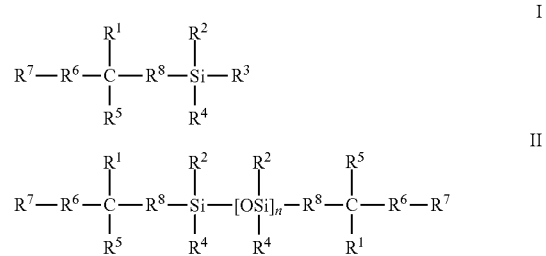

wherein:

n is an integer between 3 and 35, and preferably between 4 and 25;

$R^1$ is hydrogen, $C_{1-6}$alkyl;

$R^2$, $R^3$, and $R^4$, are independently, $C_{1-6}$alkyl, tri$C_{1-6}$alkylsiloxy, phenyl, naphthyl, substituted $C_{1-6}$alkyl, substituted phenyl, or substituted naphthyl where the alkyl substitutents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl, and where the aromatic substitutents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl;

$R^5$ is hydroxyl, an alkyl group containing one or more hydroxyl groups; or $(CH_2(CR^9R^{10})_yO)_x)$—$R^{11}$ wherein y is 1 to 5, preferably 1 to 3, x is an integer of 1 to 100, preferably 2 to 90 and more preferably 10 to 25; $R^9$-$R^{11}$ are independently selected from H, alkyl having up to 10 carbon atoms and alkyls having up to 10 carbon atoms substituted with at least one polar functional group, $R^6$ is a divalent group comprising up to 20 carbon atoms;

$R^7$ is a monovalent group that can under free radical and/or cationic polymerization and comprising up to 20 carbon atoms $R^8$ is a divalent or trivalent group comprising up to 20 carbon atoms.

Reaction mixtures of the present invention may include more than one hydroxyl-functionalized silicone containing monomer.

For monofunctional hydroxyl functionalized silicone containing monomer the preferred $R^1$ is hydrogen, and the preferred $R^2$, $R^3$, and $R^4$, are $C_{1-6}$alkyl and tri$C_{1-6}$alkylsiloxy, most preferred methyl and trimethylsiloxy. For multifunctional (difunctional or higher) $R^1$-$R^4$ independently comprise ethylenically unsaturated polymerizable groups and more preferably comprise an acrylate, a styryl, a $C_{1-6}$alkylacrylate, acrylamide, $C_{1-6}$alkylacrylamide, N-vinyllactam, N-vinylamide, $C_{2-12}$ alkenyl, $C_{2-12}$alkenylphenyl, $C_{2-12}$alkenylnaphthyl, or $C_{2-6}$alkenylphenyl$C_{1-6}$alkyl.

The preferred $R^5$ is hydroxyl, —CH$_2$OH or CH$_2$CHOHCH$_2$OH, with hydroxyl being most preferred.

The preferred $R^6$ is a divalent $C_{1-6}$alkyl, $C_{1-6}$alkyloxy, $C_{1-6}$alkoxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl. The particularly preferred $R^6$ is a divalent methyl (methylene).

The preferred $R^7$ comprises a free radical reactive group, such as an acrylate, a styryl, vinyl, vinyl ether, itaconate group, a $C_{1-6}$alkylacrylate, acrylamide, $C_{1-6}$alkylacrylamide, N-vinyllactam, N-vinylamide, $C_{2-12}$alkenyl, $C_{2-12}$alkenylphenyl, $C_{2-12}$alkenylnaphthyl, or $C_{2-6}$alkenylphenyl $C_{1-6}$alkyl or a cationic reactive group such as vinyl ether or epoxide groups. The particularly preferred $R^7$ is methacrylate.

The preferred $R^8$ is a divalent $C_{1-6}$alkyl, $C_{1-6}$alkyloxy, $C_{1-6}$alkoxy$C_{1-6}$alkyl, phenylene, naphthalene, $C_{1-12}$cycloalkyl, $C_{1-6}$alkoxycarbonyl, amide, carboxy, $C_{1-6}$alkylcarbonyl, carbonyl, $C_{1-6}$alkoxy, substituted $C_{1-6}$alkyl, substituted $C_{1-6}$alkyloxy, substituted $C_{1-6}$alkyloxy$C_{1-6}$alkyl, substituted phenylene, substituted naphthalene, substituted $C_{1-12}$cycloalkyl, where the substituents are selected from one or more members of the group consisting of $C_{1-6}$alkoxycarbonyl, $C_{1-6}$alkyl, $C_{1-6}$alkoxy, amide, halogen, hydroxyl, carboxyl, $C_{1-6}$alkylcarbonyl and formyl. The particularly preferred $R^8$ is $C_{1-6}$alkyloxy$C_{1-6}$alkyl.

Examples of hydroxyl-functionalized silicone containing monomer of Formula I that are particularly preferred are 2-propenoic acid, 2-methyl-,2-hydroxy-3-[3-[1,3,3,3-tetramethyl-1-[(trimethylsilyl)oxy]disiloxanyl]propoxy]propyl ester (which can also be named (3-methacryloxy-2-hydroxypropyloxy)propylbis(trimethylsiloxy)methylsilane)

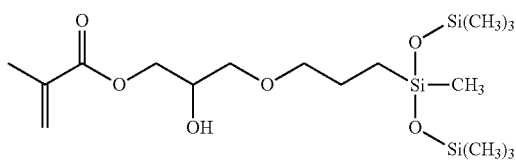

The above compound, (3-methacryloxy-2-hydroxypropyloxy)propylbis(trimethylsiloxy)methylsilane is formed from an epoxide, which produces an 80:20 mixture of the compound shown above and (2-methacryloxy-3-hydroxypropyloxy)propylbis(trimethylsiloxy)methylsilane. In some embodiments of the present invention it is preferred to have some amount of the primary hydroxyl present, preferably greater than about 10 wt % and more preferably at least about 20 wt %.

Other suitable hydroxyl-functionalized silicone containing monomers include (3-methacryloxy-2-hydroxypropyloxy)propyltris(trimethylsiloxy)silane

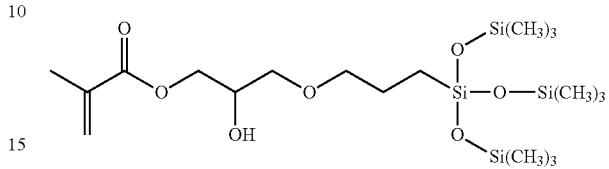

bis-3-methacryloxy-2-hydroxypropyloxypropyl polydimethylsiloxane

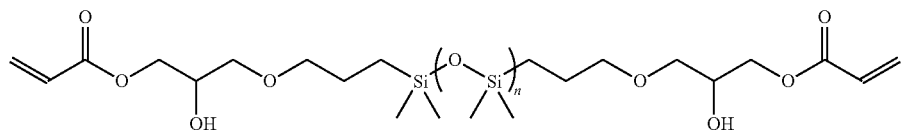

3-methacryloxy-2-(2-hydroxyethoxy)propyloxy)propylbis(trimethylsiloxy)methylsilane

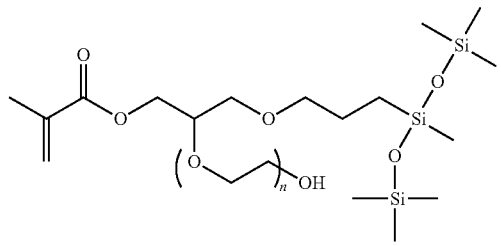

N,N,N',N'-tetrakis(3-methacryloxy-2-hydroxypropyl)-α,ω-bis-3-aminopropyl-polydimethylsiloxane The reaction products of glycidyl methacrylate with amino-functional polydimethylsiloxanes may also be used as a hydroxyl-functional silicone containing monomer. Other suitable hydroxyl-functional silicone containing monomers include those disclosed in columns 6, 7 and 8 of U.S. Pat. No. 5,994,488, and monomers disclosed in U.S. Pat. Nos. 4,259,467; 4,260,725; 4,261,875; 4,649,184; 4,139,513, 4,139,692, US 2002/0016383, U.S. Pat. Nos. 4,139,513 and 4,139,692. These and any other patents or applications cited herein are incorporated by reference.

Still additional structures which may be suitable hydroxyl-functionalized silicone containing monomers include those similar to the compounds disclosed in Pro. ACS Div. Polym. Mat. Sci. Eng., Apr. 13-17, 1997, p. 42, and having the following structure:

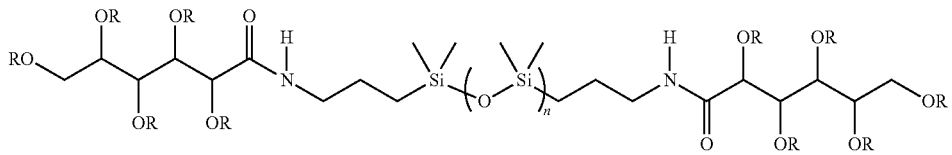

where n=1-50 and R independently comprise H or a polymerizable unsaturated group, with at least one R comprising a polymerizable group, and at least one R, and preferably 3-8 R, comprising H.

Additional suitable hydroxyl-functionalized silicone containing monomers are disclosed in U.S. Pat. No. 4,235,985. These components may be removed from the hydroxyl-functionalized monomer via known methods such as liquid phase chromatography, distillation, recrystallization or extraction, or their formation may be avoided by careful selection of reaction conditions and reactant ratios.

Suitable monofunctional hydroxyl-functionalized silicone monomers are commercially available from Gelest, Inc. Morrisville, Pa. Suitable multifunctional hydroxyl-functionalized silicone monomers are commercially available from Gelest, Inc, Morrisville, Pa. or may be made using the procedures disclosed in U.S. Pat. Nos. 5,994,488 and 5,962, 548. Suitable PEG type hydroxyl-functionalized silicone monomers may be made using the procedures disclosed in PCT/JP02/02231.

While hydroxyl-functionalized silicone containing monomers have been found to be particularly suitable for providing compatible polymers for biomedical devices, and particularly ophthalmic devices, any functionalized silicone containing monomer which, when polymerized and/or formed into a final article is compatible with the selected hydrophilic components may be used. Suitable functionalized silicone containing monomers may be selected using the following monomer compatibility test. In this test one gram of each of mono-3-methacryloxypropyl terminated, mono-butyl terminated polydimethylsiloxane (mPDMS MW 800-1000) and a monomer to be tested are mixed together in one gram of 3,7-dimethyl-3-octanol at about 20° C. A mixture of 12 weight parts K-90 PVP and 60 weight parts DMA is added dropwise to hydrophobic component solution, with stirring, until the solution remains cloudy after three minutes of stirring. The mass of the added blend of PVP and DMA is determined in grams and recorded as the monomer compatibility index. Any hydroxyl-functionalized silicone-containing monomer having a compatibility index of greater than 0.2 grams, more preferably greater than about 0.7 grams and most preferably greater than about 1.5 grams will be suitable for use in this invention.

An "effective amount" or a "compatibilizing effective amount" of the hydroxyl-functionalized silicone-containing monomers of the invention is the amount needed to compatibilize or dissolve the high molecular weight hydrophilic polymer and the other components of the polymer formulation. Thus, the amount of hydroxyl-functional silicone containing monomer will depend in part on the amount of hydrophilic polymer which is used, with more hydroxyl-functionalized silicone containing monomer being needed to compatibilize higher concentrations of hydrophilic polymer. Effective amounts of hydroxyl-functionalized silicone containing monomer in the polymer formulation include about 5% (weight percent, based on the weight percentage of the reactive components) to about 90%, preferably about 10% to about 80%, most preferably, about 20% to about 50%.

In addition to the high molecular weight hydrophilic polymers and the hydroxyl-functionalized silicone containing monomers of the invention other hydrophilic and hydrophobic monomers, crosslinkers, additives, diluents, polymerization initiators may be used to prepare the biomedical devices of the invention. In addition to high molecular weight hydrophilic polymer and hydroxyl-functionalized silicone containing monomer, the hydrogel formulations may include additional silicone containing monomers, hydrophilic monomers, and cross linkers to give the biomedical devices of the invention.

Additional Silicone Containing Monomers

With respect to the additional silicone containing monomers, amide analogs of TRIS described in U.S. Pat. No. 4,711,943, vinylcarbamate or carbonate analogs described in U.S. Pat. No. 5,070,215, and siloxane containing monomers contained in U.S. Pat. No. 6,020,445 are useful and these aforementioned patents as well as any other patents mentioned in this specification are hereby incorporated by reference. More specifically, 3-methacryloxypropyltris(trimethylsiloxy)silane (TRIS), monomethacryloxypropyl terminated polydimethylsiloxanes, polydimethylsiloxanes, 3-methacryloxypropylbis(trimethylsiloxy)methylsilane, methacryloxypropylpentamethyl disiloxane and combinations thereof are particularly useful as additional silicone-containing monomers of the invention. Additional silicone containing monomers may be present in amounts of about 0 to about 75 wt %, more preferably of about 5 and about 60 and most preferably of about 10 and 40 weight %.

Hydrophilic Monomers

Additionally, reaction components of the present invention may also include any hydrophilic monomers used to prepare conventional hydrogels. For example monomers containing acrylic groups ($CH_2=CRCOX$, where R is hydrogen or $C_{1-6}$alkyl an X is O or N) or vinyl groups ($-C=CH_2$) may be used. Examples of additional hydrophilic monomers are N,N-dimethylacrylamide, 2-hydroxyethyl methacrylate, glycerol monomethacrylate, 2-hydroxyethyl methacrylamide, polyethyleneglycol monomethacrylate, methacrylic acid, acrylic acid, N-vinyl pyrrolidone, N-vinyl-N-methyl acetamide, N-vinyl-N-ethyl acetamide, N-vinyl-N-ethyl formamide, N-vinyl formamide and combinations thereof.

Aside the additional hydrophilic monomers mentioned above, polyoxyethylene polyols having one or more of the terminal hydroxyl groups replaced with a functional group containing a polymerizable double bond may be used. Examples include polyethylene glycol, as disclosed in U.S. Pat. No. 5,484,863, ethoxylated alkyl glucoside, as disclosed in U.S. Pat. No. 5,690,953, U.S. Pat. No. 5,304,584, and ethoxylated bisphenol A, as disclosed in U.S. Pat. No. 5,565,539, reacted with one or more molar equivalents of an end-capping group such as isocyanatoethyl methacrylate, methacrylic anhydride, methacryloyl chloride, vinylbenzoyl chloride, and the like, produce a polyethylene polyol having one or more terminal polymerizable olefinic groups bonded to the polyethylene polyol through linking moieties such as carbamate, urea or ester groups.

Still further examples include the hydrophilic vinyl carbonate or vinyl carbamate monomers disclosed in U.S. Pat. No. 5,070,215, the hydrophilic oxazolone monomers disclosed in U.S. Pat. No. 4,910,277, the disclosures of which are incorporated herein by reference and polydextran.

The preferred additional hydrophilic monomers are N,N-dimethylacrylamide (DMA), 2-hydroxyethyl methacrylate (HEMA), glycerol methacrylate, 2-hydroxyethyl methacrylamide, N-vinylpyrrolidone (NVP), polyethyleneglycol monomethacrylate, methacrylic acid, acrylic acid and combinations thereof, with hydrophilic monomers comprising DMA being particularly preferred. Additional hydrophilic monomers may be present in amounts of about 0 to about 70 wt %, more preferably of about 5 and about 60 and most preferably of about 10 and 50 weight %.

Crosslinkers

Suitable crosslinkers are compounds with two or more polymerizable functional groups. The crosslinker may be hydrophilic or hydrophobic and in some embodiments of the present invention mixtures of hydrophilic and hydrophobic crosslinkers have been found to provide silicone hydrogels with improved optical clarity (reduced haziness compared to a CSI Thin Lens). Examples of suitable hydrophilic crosslinkers include compounds having two or more polymerizable functional groups, as well as hydrophilic functional groups such as polyether, amide or hydroxyl groups. Specific examples include TEGDMA (tetraethyleneglycol dimethacrylate), TrEGDMA (triethyleneglycol dimethacrylate), ethyleneglycol dimethacrylate (EGDMA), ethylenediamine dimethylacrylamide, glycerol dimethacrylate and combinations thereof Examples of suitable hydrophobic crosslinkers include multifunctional hydroxyl-functionalized silicone containing monomer, multifunctional polyether-polydimethylsiloxane block copolymers, combinations thereof and the like. Specific hydrophobic crosslinkers include acryloxypropyl terminated polydimethylsiloxane (n=10 or 20) (acP-DMS), hydroxylacrylate functionalized siloxane macromer, methacryloxypropyl terminated PDMS, butanediol dimethacrylate, divinyl benzene, 1,3-bis(3-methacryloxypropyl) tetrakis(trimethylsiloxy) disiloxane and mixtures thereof. Preferred crosslinkers include TEGDMA, EGDMA, acP-DMS and combinations thereof. The amount of hydrophilic crosslinker used is generally about 0 to about 2 weight % and preferably from about 0.5 to about 2 weight % and the amount of hydrophobic crosslinker is about 0 to about 5 weight %, which can alternatively be referred to in mol % of about 0.01 to about 0.2 mmole/gm reactive components, preferably about 0.02 to about 0.1 and more preferably 0.03 to about 0.6 mmole/gm.

Increasing the level of crosslinker in the final polymer has been found to reduce the amount of haze. However, as crosslinker concentration increases above about 0.15 mmole/gm reactive components modulus increases above generally desired levels (greater than about 90 psi). Thus, in the present invention the crosslinker composition and amount is selected to provide a crosslinker concentration in the reaction mixture of between about 0.01 and about 0.1 mmoles/gm crosslinker.

Additional components or additives, which are generally known in the art may also be included. Additives include but are not limited to ultra-violet absorbing compounds and monomer, reactive tints, antimicrobial compounds, pigments, photochromic, release agents, combinations thereof and the like.

Additional components include other oxygen permeable components such as carbon-carbon triple bond containing monomers and fluorine containing monomers which are known in the art and include fluorine-containing (meth)acrylates, and more specifically include, for example, fluorine-containing $C_2$-$C_{12}$ alkyl esters of (meth)acrylic acid such as 2,2,2-trifluoroethyl (meth)acrylate, 2,2,2,2',2',2'-hexafluoroisopropyl (meth)acrylate, 2,2,3,3,4,4,4-heptafluorobutyl (meth)acrylate, 2,2,3,3,4,4,5,5,6,6,7,7,8,8,8-pentadecafluorooctyl (meth)acrylate, 2,2,3,3,4,4,5,5,6,6,7,7,8,8,9,9-hexadecafluorononyl (meth)acrylate and the like Diluents The reaction components (hydroxyl-functionalized silicone containing monomer, hydrophilic polymer, crosslinker (s) and other components) are generally mixed and reacted in the absence of water and optionally, in the presence of at least one diluent to form a reaction mixture. The type and amount of diluent used also effects the properties of the resultant polymer and article. The haze and wettability of the final article may be improved by selecting relatively hydrophobic diluents and/or decreasing the concentration of diluent used. As discussed above, increasing the hydrophobicity of the diluent may also allow poorly compatible components (as measured by the compatibility test) to be processed to form a compatible polymer and article. However, as the diluent becomes more hydrophobic, processing steps necessary to replace the diluent with water will require the use of solvents other than water. This may undesirably increase the complexity and cost of the manufacturing process. Thus, it is important to select a diluent which provides the desired compatibility to the components with the necessary level of processing convenience. Diluents useful in preparing the devices of this invention include ethers, esters, alkanes, alkyl halides, silanes, amides, alcohols and combinations thereof. Amides and alcohols are preferred diluents, and secondary and tertiary alcohols are most preferred alcohol diluents. Examples of ethers useful as diluents for this invention include tetrahydrofuran, tripropylene glycol methyl ether, dipropylene glycol methyl ether, ethylene glycol n-butyl ether, diethylene glycol n-butyl ether, diethylene glycol methyl ether, ethylene glycol phenyl ether, propylene glycol methyl ether, propylene glycol methyl ether acetate, dipropylene glycol methyl ether acetate, propylene glycol n-propyl ether, dipropylene glycol n-propyl ether, tripropylene glycol n-butyl ether, propylene glycol n-butyl ether, dipropylene glycol n-butyl ether, tripropylene glycol n-butyl ether, propylene glycol phenyl ether dipropylene glycol dimethyl ether, polyethylene glycols, polypropylene glycols and mixtures thereof. Examples of esters useful for this invention include ethyl acetate, butyl acetate, amyl acetate, methyl lactate, ethyl lactate, i-propyl lactate. Examples of alkyl halides useful as diluents for this invention include methylene chloride. Examples of silanes useful as diluents for this invention include octamethylcyclotetrasiloxane.

Examples of alcohols useful as diluents for this invention include those having the formula

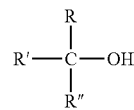

wherein R, R' and R" are independently selected from H, a linear, branched or cyclic monovalent alkyl having 1 to 10 carbons which may optionally be substituted with one or more groups including halogens, ethers, esters, aryls, amines, amides, alkenes, alkynes, carboxylic acids, alcohols, aldehydes, ketones or the like, or any two or all three of R, R and R" can together bond to form one or more cyclic structures, such as alkyl having 1 to 10 carbons which may also be substituted as just described, with the proviso that no more than one of R, R' or R" is H.

It is preferred that R, R' and R" are independently selected from H or unsubstituted linear, branched or cyclic alkyl groups having 1 to 7 carbons. It is more preferred that R, R', and R" are independently selected form unsubstituted linear, branched or cyclic alkyl groups having 1 to 7 carbons. In certain embodiments, the preferred diluent has 4 or more, more preferably 5 or more total carbons, because the higher molecular weight diluents have lower volatility, and lower flammability. When one of the R, R' and R" is H, the structure forms a secondary alcohol. When none of the R, R' and R" are H, the structure forms a tertiary alcohol. Tertiary alcohols are more preferred than secondary alcohols. The diluents are preferably inert and easily displaceable by water when the total number of carbons is five or less.

Examples of useful secondary alcohols include 2-butanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, and the like.

Examples of useful tertiary alcohols include tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, and the like.

A single alcohol or mixtures of two or more of the above-listed alcohols or two or more alcohols according to the structure above can be used as the diluent to make the polymer of this invention.

In certain embodiments, the preferred alcohol diluents are secondary and tertiary alcohols having at least 4 carbons. The more preferred alcohol diluents include tert-butanol, tert-amyl alcohol, 2-butanol, 2-methyl-2-pentanol, 2,3-dimethyl-2-butanol, 3-methyl-3-pentanol, 3-ethyl-3-pentanol, 3,7-dimethyl-3-octanol.

Presently, the most preferred diluents are hexanol, heptanol, octanol, nonanol, decanol, tert-butyl alcohol, 3-methyl-3-pentanol, isopropanol, t amyl alcohol, ethyl lactate, methyl lactate, i-propyl lactate, 3,7-dimethyl-3-octanol, dimethyl formamide, dimethyl acetamide, dimethyl propionamide, N methyl pyrrolidinone and mixtures thereof. Additional diluents useful for this invention are disclosed in U.S. Pat. No. 6,020,445, which is incorporated herein by reference.

In one embodiment of the present invention the diluent is water soluble at processing conditions and readily washed out of the lens with water in a short period of time. Suitable water soluble diluents include 1-ethoxy-2-propanol, 1-methyl-2-propanol, t-amyl alcohol, tripropylene glycol methyl ether, isopropanol, 1-methyl-2-pyrrolidone, N,N-dimethylpropionamide, ethyl lactate, dipropylene glycol methyl ether, mixtures thereof and the like. The use of a water soluble diluent allows the post molding process to be conducted using water only or aqueous solutions which comprise water as a substantial component.

In one embodiment, the amount of diluent is generally less than about 50 weight % of the reaction mixture and preferably less than about 40% and more preferably between about 10 and about 30%.

The diluent may also comprise additional components such as release agents. Suitable release agents are water soluble and aid in lens deblocking.

The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acyl phosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4,4-trimethylpentyl phosphine oxide (DMBAPO), bis(2,4,6-trimethylbenzoyl)-phenylphosphineoxide (Irgacure 819), 2,4,6-trimethylbenzyldiphenyl phosphine oxide and 2,4,6-trimethylbenzyoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiator is a combination of 1-hydroxycyclohexyl phenyl ketone and bis(2,6-dimethoxybenzoyl)-2,4-4-trimethylpentyl phosphine oxide (DMBAPO), and the preferred method of polymerization initiation is visible light. The most preferred is bis(2,4,6-trimethylbenzoyl)-phenylphosphineoxide (Irgacure 819®).

The invention further comprises, consists and consists essentially of a silicone hydrogel, biomedical device, ophthalmic device and contact lenses of the formulae shown below:

| Wt % components | | | |
|---|---|---|---|
| HFSCM | HMWHP | SCM | HM |
| 5-90 | 1-15, 3-15 or 5-12 | 0 | 0 |
| 10-80 | 1-15, 3-15 or 5-12 | 0 | 0 |
| 20-50 | 1-15, 3-15 or 5-12 | 0 | 0 |
| 5-90 | 1-15, 3-15 or 5-12 | 0-80, 5-60 or 10-40 | 0-70, 5-60 or 10-50 |
| 10-80 | 1-15, 3-15 or 5-12 | 0-80, 5-60 or 10-40 | 0-70, 5-60 or 10-50 |
| 20-50 | 1-15, 3-15 or 5-12 | 0-80, 5-60 or 10-40 | 0-70, 5-60 or 10-50 |

HFSCM is hydroxyl-functionalized silicone containing monomer
HMWHP is high molecular weight hydrophilic polymer
SCM is silicone containing monomer
HM is hydrophilic monomer The weight percents above are based upon all reactive components. Thus, the present invention includes silicone hydrogel, biomedical device, ophthalmic device and contact lenses having each of the composition listed in the table, which describes ninety possible compositional ranges. Each of the ranges listed above is prefaced by the word "about". The foregoing range combinations are presented with the proviso that the listed components, and any additional components add up to 100 weight %.

A preferred range of the combined silicone-containing monomers (hydroxyl-functionalized silicone-containing and additional silicone-containing monomers) is from about 5 to 99 weight percent, more preferably about 15 to 90 weight percent, and most preferably about 25 to about 80 weight percent of the reaction components. A preferred range of hydroxyl-functionalized silicone-containing monomer is about 5 to about 90 weight percent, preferably about 10 to about 80, and most preferably about 20 to about 50 weight percent. A preferred range of hydrophilic monomer is from about 0 to about 70 weight percent, more preferably about 5 to about 60 weight percent, and most preferably about 10 to about 50 weight percent of the reactive components. A preferred range of high molecular weight hydrophilic polymer is about 1 to about 15 weight percent, more preferably about 3 to about 15 weight percent, and most preferably about 5 to about 12 weight percent. All of the about weight percents are based upon the total of all reactive components A preferred range of diluent is from about 0 to about 70 weight percent, more preferably about 0 to about 50 weight percent, and still more preferably about 0 to about 40 weight percent and in some embodiments, most preferably between about 10 and about 30 weight percent, based upon the weight all component in the reactive mixture. The amount of diluent required varies depending on the nature and relative amounts of the reactive components.

In a preferred embodiment, the reactive components comprise 2-propenoic acid, 2-methyl-,2-hydroxy-3-[3-[1,3,3,3-tetramethyl-1-[(trimethylsilyl)oxy]disiloxanyl]propoxy] propyl ester "SiGMA" (~28 wgt. % of the reaction components); (800-1000 MW monomethacryloxypropyl terminated mono-n-butyl terminated polydimethylsiloxane, "mPDMS" (~31% wt), N,N-dimethylacrylamide, "DMA" (~24% wt), 2-hydroxyethyl methacrylate, "HEMA" (~6% wt), tetraethyleneglycoldimethacrylate, "TEGDMA" (~1.5% wt), polyvinylpyrrolidone, "K-90 PVP" (~7% wt), with the balance comprising minor amounts of additives and photoinitiators. The polymerization is most preferably conducted in the presence of about 23% (weight % of the combined monomers and diluent blend) 3,7-dimethyl-3-octanol diluent.

In other preferred embodiments the reactive components comprise those shown in the Table below. All amounts are prefaced by the word "about".

| Component | Wt % | |
| --- | --- | --- |
| SiGMA | 30 | 30 |
| mPDMS | 23 | 18 |
| DMA | 31 | 31 |
| HEMA | 7.5 | 9 |
| EGDMA | 0.75 | 0.8 |
| PVP | 6 | 6 |

The polymerizations for the above formulations are preferably conducted in the presence of tert-amyl-alcohol as a diluent comprising about 29 weight percent of the uncured reaction mixture.

Processing

The biomedical devices of the invention are prepared by mixing the high molecular weight hydrophilic polymer, the hydroxyl-functionalized silicone-containing monomer, plus one or more of the following: the additional silicone-containing monomers, the hydrophilic monomers, the additives ("reactive components"), and the diluents ("reaction mixture"), with a polymerization initiator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses comprising the polymer of this invention is by the molding of the silicone hydrogels, which is economical, and enables precise control over the final shape of the hydrated lens. For this method, the reaction mixture is placed in a mold having the shape of the final desired silicone hydrogel, i.e., water-swollen polymer, and the reaction mixture is subjected to conditions whereby the monomers polymerize, to thereby produce a polymer/diluent mixture in the shape of the final desired product. Then, this polymer/diluent mixture is treated with a solvent to remove the diluent and ultimately replace it with water, producing a silicone hydrogel having a final size and shape which are quite similar to the size and shape of the original molded polymer/diluent article. This method can be used to form contact lenses and is further described in U.S. Pat. Nos. 4,495,313; 4,680,336; 4,889,664; and 5,039,459, incorporated herein by reference.

Curing

Yet another feature of the present invention is a process for curing silicone hydrogel formulations to provide enhanced wettability. It has been found that the gel time for a silicone hydrogel may be used to select cure conditions which provide a wettable ophthalmic device, and specifically a contact lens. The gel time is the time at which a crosslinked polymer network is formed, resulting in the viscosity of the curing reaction mixture approaching infinity and the reaction mixture becoming non-fluid. The gel point occurs at a specific degree of conversion, independent of reaction conditions, and therefore can be used as an indicator of the rate of the reaction. It has been found that, for a given reaction mixture, the gel time may be used to determine cure conditions which impart desirable wettability. Thus, in a process of the present invention, the reaction mixture is cured at or above a gel time that provides improved wettability, or more preferably sufficient wettability for the resulting device to be used without a hydrophilic coating or surface treatment ("minimum gel time"). Preferably improved wettability is a decrease in advancing dynamic contact angle of at least 10% compared to formulation with no high molecular weight polymer. Longer gel times are preferred as they provide improved wettability and increased processing flexibility.

Gel times will vary for different silicone hydrogel formulations. Cure conditions also effect gel time. For example the concentration of crosslinker will impact gel time, increasing crosslinker concentrations decreases gel time. Increasing the intensity of the radiation (for photopolymerization) or temperature (for thermal polymerization), the efficiency of initiation (either by selecting a more efficient initiator or irradiation source, or an initiator which absorbs more strongly in the selected irradiation range) will also decrease gel time. Temperature and diluent type and concentration also effect gel time in ways understood by those of skill in the art.

The minimum gel time may be determined by selecting a given formulation, varying one of the above factors and measuring the gel time and contact angles. The minimum gel time is the point above which the resulting lens is generally wettable. Below the minimum gel time the lens is generally not wettable. For a contact lens "generally wettable" is a lens which displays an advancing dynamic contact angle of less than about 80°, preferably less than 70° and more preferably less than about 60° or a contact lens which displays a tear film break up time equal to or better than an ACUVUE® lens. Thus, those of skill in the art will appreciate that minimum gel point as defined herein may be a range, taking into consideration statistical experimental variability.

In certain embodiments using visible light irradiation minimum gel times of at least about 30 seconds, preferably at least about 35 seconds, and more preferably greater than about 40 seconds have been found to be advantageous.

The mold containing the reaction mixture is exposed to ionizing or actinic radiation, for example electron beams, Xrays, UV or visible light, ie. electromagnetic radiation or particle radiation having a wavelength in the range of from about 150 to about 800 nm. Preferably the radiation source is UV or visible light having a wavelength of about 250 to about 700 nm. Suitable radiation sources include UV lamps, fluorescent lamps, incandescent lamps, mercury vapor lamps, and sunlight. In embodiments where a UV absorbing compound is included in the composition (for example, as a UV block) curing is conducting by means other than UV irradiation (such as by visible light or heat). In a preferred embodiment the radiation source is selected from UVA (about 315-about 400 nm), UVB (about 280-about 315) or visible light (about 400-about 450 nm), at low intensity. In another preferred embodiment, the reaction mixture includes a UV absorbing compound, is cured using visible light and low intensity. As used herein the term "low intensity" means those between about 0.1 mW/cm$^2$ to about 6 mW/cm$^2$ and preferably between about 0.2 mW/cm$^2$ and 3 mW/cm$^2$. The cure time is long, generally more than about 1 minute and preferably between about 1 and about 60 minutes and still more preferably between about 1 and about 30 minutes This slow, low intensity cure is critical to providing compatible ophthalmic devices which display lasting resistance to protein deposition in vivo.

The temperature at which the reaction mixture is cured is also important. As the temperature is increased above ambient the haze of the resulting polymer decreases. Temperatures effective to reduce haze include temperatures at which the haze for the resulting lens is decreased by at least about 20% as compared to a lens of the same composition made at 25° C. Thus, suitable cure temperatures include those greater than about 25° C., preferably those between about 25° C. and 70° C. and more preferably those between about 40° C. and 70° C. The precise set of cure conditions (temperature, intensity and time) will depend upon the components of lens material selected and, with reference to the teaching herein, are within the skill of one of ordinary skill in the art to determine. Cure may be conducted in one or a multiplicity of cure zones.

The cure conditions must be sufficient to form a polymer network from the reaction mixture. The resulting polymer network is swollen with the diluent and has the form of the mold cavity.

Deblocking

After the lenses have been cured they are preferably removed from the mold. Unfortunately, the silicone components used in the lens formulation render the finished lenses "sticky" and difficult to release from the lens molds. Lenses can be deblocked (removed from the mold half or tool supporting the lens) using a solvent, such as an organic solvent. However, in one embodiment of the present invention at least one low molecular weight hydrophilic polymer is added to the reaction mixture, the reaction mixture is formed into the desired article, cured and deblocked in water or an aqueous solution comprising, consisting essentially of and consisting of a small amount of surfactant. The low molecular weight hydrophilic polymer can be any polymer having a structure as defined for a high molecular weight polymer, but with a molecular weight such that the low molecular weight hydrophilic polymer extracts or leaches from the lens under deblocking conditions to assist in lens release from the mold. Suitable molecular weights include those less than about 40,000 Daltons, preferably between less than about 20,000 Daltons. Those of skill in the art will appreciate that the foregoing molecular weights are averages, and that some amount of material having a molecular weight higher than the given averages may be suitable, so long as the average molecular weight is within the specified range. Preferably the low molecular weight polymer is selected from water soluble polyamides, lactams and polyethylene glycols, and mixtures thereof and more preferably polyvinylpyrrolidone, polyethylene glycols, poly 2 ethyl-2-oxazoline (available from Polymer Chemistry Innovations, Tucson, Ariz.), poly(methacrylic acid), poly(l-lactic acid), polycaprolactam, polycaprolactone, polycaprolactone diol, polyvinyl alcohol, poly(2-hydroxyethyl methacrylate), poly (acrylic acid), poly(l-glycerol methacrylate), poly(2-ethyl-2-oxazoline), poly(2-hydroxypropyl methacrylate), poly(2-vinylpyridine N-oxide), polyacrylamide, polymethacrylamide mixtures there of and the like.

The low molecular weight hydrophilic polymer may be used in amounts up to about 20 wt %, more preferably in amounts between about 5 and about 20 wt % based upon the total weight of the reactive components.

Suitable surfactants include non-ionic surfactants including betaines, amine oxides, combinations thereof and the like. Examples of suitable surfactants include TWEEN® (ICI), DOE 120 (Amerchol/Union Carbide) and the like. The surfactants may be used in amounts up to about 10,000, preferably between about 25 and about 1500 ppm and more preferably between about 100 ppm and about 1200 ppm.

Suitable release agents are low molecular weight, and include 1-methyl-4-piperidone, 3-morpholino-1,2-propanediol, tetrahydro-2H-pyran-4-ol, glycerol formal, ethyl-4-oxo-1-piperidine carboxylate, 1,3-dimethyl-3,4,5,6-tetrahydro-2(1H)-pyrimidinone and 1-(2-hydroxyethyl)-2-pyrrolidone.

Lenses made from reaction mixtures without low molecular weight hydrophilic polymer may be deblocked in an aqueous solution comprising at least one organic solvent. Suitable organic solvents are hydrophobic, but miscible with water. Alcohols, ethers and the like are suitable, more specifically primary alcohols and more specifically isopropyl alcohol, DPMA, TPM, DPM, methanol, ethanol, propanol and mixtures thereof being suitable examples.

Suitable deblocking temperatures range from about ambient to about 100° C., preferably between about 70° C. and 95° C., with higher temperatures providing quicker deblocking times. Agitation, such as by sonication, may also be used to decrease deblocking times. Other means known in the art, such as vacuum nozzles may also be used to remove the lenses from the molds.

Diluent Replacement/Hydration

Typically after curing the reaction mixture, the resulting polymer is treated with a solvent to remove the diluent (if used), unreacted components, byproducts, and the like and hydrate the polymer to form the hydrogel. Alternatively, depending on the solubility characteristics of the hydrogel's components, the solvent initially used can be an organic liquid such as ethanol, methanol, isopropanol, TPM, DPM, PEGs, PPGs, glycerol, mixtures thereof, or a mixture of one or more such organic liquids with water, followed by extraction with pure water (or physiological saline). The organic liquid may also be used as a "pre-soak". After demolding (removing the back curve from the lens), lenses may be briefly soaked (times up to about 30 minutes, preferably between about 5 and about 30 minutes) in the organic liquid or a mixture of organic liquid and water. After the pre-soak, the lens may be further hydrated using aqueous extraction solvents.

In some embodiments, the preferred process uses an extraction solvent that is predominately water, preferably greater than 90% water, more preferably greater than 97% water. Other components may includes salts such as sodium chloride, sodium borate boric acid, DPM, TPM, ethanol or isopropanol. Lenses are generally released from the molds into this extraction solvent, optionally with stirring or a continuous flow of the extraction solvent over the lenses. This process can be conducted at temperatures from about 2 to about 121° C., preferably from about 20 to about 98° C. The process can be conducted at elevated pressures, particularly when using temperatures in excess of about 100° C., but is more typically conducted at ambient pressures. It is possible to deblock the lenses into one solution (for example containing some release aid) and then transfer them into another (for example the final packing solution), although it may also be possible to deblock the lenses into the same solution in which they are packaged. The treatment of lenses with this extraction solvent may be conducted for a period of from about 30 seconds to about 3 days, preferably between about 5 and about 30 minutes. The selected hydration solution may additional comprise small amounts of additives such as surfactants. Suitable surfactants include non-ionic surfactants, such as betaines and amine oxides. Specific surfactants include TWEEN 80 (available from Amerchol), DOE 120 (available from Union Carbide), Pluronics, methyl cellulose, mixtures thereof and the like and may be added in amounts between about 0.01 weight % and about 5 weight % % based upon total weight of hydration solution used.

In one embodiment the lenses may be hydrated using a "step down" method, where the solvent is replaced in steps over the hydration process. Suitable step down processes have at least two steps, where a percentage of the solvent is replaced with water.

The silicone hydrogels after hydration of the polymers preferably comprise about 10 to about 60 weight percent water, more preferably about 20 to about 55 weight percent water, and most preferably about 25 to about 50 weight percent water of the total weight of the silicone hydrogel. Further details on the methods of producing silicone hydrogel contact lenses are disclosed in U.S. Pat. Nos. 4,495,313; 4,680,336; 4,889,664; and 5,039,459, which are hereby incorporated by reference.

The cured ophthalmic device of the present invention displays excellent resistance to fouling in vivo, without a coating. When the biomedical device is an ophthalmic device, resistance to biofouling may be measured by measuring the amount of surface deposits on the lens during the wear period, often referred to as "lipid deposits".

Lens surface deposits are measured as follows: Lenses are put on human eyes and evaluated after 30 minutes and one week of wear using a slit lamp. During the evaluation the patient is asked to blink several times and the lenses are manually "pushed" in order to differentiate between deposits and back surface trapped debris. Front and back surface deposits are graded as being discrete (i.e. jelly bumps) or filmy. Front surface deposits give a bright reflection while back surface deposits do not. Deposits are differentiated from back surface trapped debris during a blink or a push-up test. The deposits will move while the back surface trapped debris will remain still. The deposits are graded into five categories based upon the percentage of the lens surface which is effected: none (< about 1%), slight (about 1 to about 5%), mild (about 6% to about 15%), moderate (about 16% to about 25%) and severe (greater than about 25%). A 10% difference between the categories is considered clinically significant.

The ophthalmic devices of the present invention also display low haze, good wettability and modulus.

Haze is measured by placing test lenses in saline in a clear cell above a black background, illuminating from below with a fiber optic lamp at an angle 66° normal to the lens cell, and capturing an image of the lens from above with a video camera. The background-subtracted scattered light image is quantitatively analyzed, by integrating over the central 10 mm of the lens, and then compared to a −1.00 diopter CSI Thin Lens®, which is arbitrarily set at a haze value of 100, with no lens set as a haze value of 0.

Wettability is measured by measuring the dynamic contact angle or DCA, typically at 23° C., with borate buffered saline, using a Wilhelmy balance. The wetting force between the lens surface and borate buffered saline is measured using a Wilhelmy microbalance while the sample is being immersed into or pulled out of the saline. The following equation is used $$F=2\gamma p \cos \theta \text{ or } \theta=\cos^{-1}(F/2\gamma p)$$

where F is the wetting force, γ is the surface tension of the probe liquid, p is the perimeter of the sample at the meniscus and θ is the contact angle. Typically, two contact angles are obtained from a dynamic wetting experiment—advancing contact angle and receding contact angle. Advancing contact angle is obtained from the portion of the wetting experiment where the sample is being immersed into the probe liquid, and these are the values reported herein. At least four lenses of each composition are measured and the average is reported.

However, DCA is not always a good predictor of wettability on eye. The pre-lens tear film non-invasive break-up time (PLTF-NIBUT) is one measure of in vivo or "clinical" lens wettability. The PLTF-NIBUT is measured using a slit lamp and a circular fluorescent tearscope for noninvasive viewing of the tearfilm (Keeler Tearscope Plus). The time elapsed between the eye opening after a blink and the appearance of the first dark spot within the tear film on the front surface of a contact lens is recorded as PLTF-NIBUT. The PLTF-NIBUT is measured 30-minutes after the lenses were placed on eye and after one week. Three measurements are taken at each time interval and were averaged into one reading. The PLTF-NIBUT is measured on both eyes, beginning with the right eye and then the left eye.

Movement is measured using the "push up" test. The patient's eyes are in the primary gaze position. The push-up test is a gentle digital push of the lens upwards using the lower lid. The resistance of the lens to upward movement is judged and graded according to the following scale: 1 (excessive, unacceptable movement), 2 (moderate, but acceptable movement), 3 (optimal movement), 4 (minimal, but acceptable movement), 5 (insufficient, unacceptable movement).

The lenses of the present invention display moduli of at least about 30 psi, preferably between about 30 and about 90 psi, and more preferably between about 40 and about 70 psi. Modulus is measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. Twelve specimens of each composition are measured and the average is reported. Tensile modulus is measured at the initial linear portion of the stress/strain curve.

The contact lenses prepared by this invention have $O_2$ Dk values between about 40 and about 300 barrer, determined by the polarographic method. Lenses are positioned on the sensor then covered on the upper side with a mesh support. The lens is exposed to an atmosphere of humidified 2.1% $O_2$. The oxygen that diffuses through the lens is measured using a polarographic oxygen sensor consisting of a 4 mm diameter gold cathode and a silver ring anode. The reference values are those measured on commercially available contact lenses using this method. Balafilcon A lenses available from Bausch & Lomb give a measurement of approx. 79 barrer. Etafilcon lenses give a measurement of 20 to 25 barrer. (1 barrer=$10^{-10}$ ($cm^3$ of gas×$cm^2$)/($cm^3$ of polymer× sec×cm Hg)).

Gel time is measured using the following method. The photopolymerization reaction is monitored with an ATS StressTech rheometer equipped with a photo-curing accessory, which consists of a temperature-controlled cell with a quartz lower plate and an aluminum upper plate, and a radiation delivery system equipped with a bandpass filter. The radiation, which originates at a Novacure mercury arc lamp equipped with an iris and computer-controlled shutter, is delivered to the quartz plate in the rheometer via a liquid light guide. The filter is a 420 nm (20 nm FWHM) bandpass filter, which simulates the light emitted from a TL03 bulb. The intensity of the radiation, measured at the surface of the quartz window with an IL1400A radiometer, using an XRL140A sensor, is controlled to ±0.02 mW/cm2 with an iris. The temperature is controlled at 45±0.1° C. After approximately 1 mL of the de-gassed reactive mixture is placed on the lower plate of the rheometer, the 25 mm diameter upper plate is lowered to 0.500±0.001 mm above the lower plate, where it is held until after the reaction reached the gel point. The sample is allowed to reach thermal equilibrium (~4 minutes, determined by the leveling-off of the steady shear viscosity) before the lamp shutter is opened and the reaction begun. During this time while the sample is reaching thermal equilibrium, the sample chamber is purged with nitrogen gas at a rate of 400 sccm. During the reaction the rheometer continuously monitors the strain resulting from an applied dynamic stress (fast oscillation mode), where time segments of less than a complete cycle are used to calculate the strain at the applied programmable stress. The computer calculates the dynamic shear modulus (G'), loss modulus (G"), and viscosity (v*), as a function of exposure time. As the reaction proceeds the shear modulus increases from <1 Pa to >0.1 MPa, and tan δ (=G"/G') drops from near infinity to less than 1. For measurements made herein the gel time is the time at which tan δ equals 1 (□□ the crossover point when G'=G"). At the time that G' reaches 100 Pa (shortly after the gel point), the restriction on the upper plate is removed so that the gap between the upper and lower plates can change as the reactive monomer mix shrinks during cure.

It will be appreciated that all of the tests specified above have a certain amount of inherent test error. Accordingly, results reported herein are not to be taken as absolute numbers, but numerical ranges based upon the precision of the particular test.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations are used in the examples below:
SiGMA 2-propenoic acid, 2-methyl-,2-hydroxy-3-[3-[1,3,3,3-tetramethyl-1-[(trimethylsilyl)oxy]disiloxanyl] propoxy]propyl ester
DMA N,N-dimethylacrylamide
HEMA 2-hydroxyethyl methacrylate
mPDMS 800-1000 MW ($M_n$) monomethacryloxypropyl terminated mono-n-butyl terminated polydimethylsiloxane
Norbloc 2-(2'-hydroxy-5-methacrylyloxyethylphenyl)-2H-benzotriazole
CGI 1850 1:1 (wgt) blend of 1-hydroxycyclohexyl phenyl ketone and bis(2,6-dimethoxybenzoyl)-2,4-4-trimethylpentyl phosphine oxide
PVP poly(N-vinyl pyrrolidone) (K value 90)
Blue HEMA the reaction product of Reactive Blue 4 and HEMA, as described in Example 4 of U.S. Pat. No. 5,944,853
IPA isopropyl alcohol
D3O 3,7-dimethyl-3-octanol
mPDMS-OH mono-(3-methacryloxy-2-hydroxypropyloxy) propyl terminated, mono-butyl terminated polydimethylsiloxane (MW 1100)
TEGDMA tetraethyleneglycol dimethacrylate
TrEGDMA triethyleneglycol dimethacrylate
TRIS 3-methacryloxypropyltris(trimethylsiloxy)silane
MPD 3-methacryloxypropyl(pentamethyldisiloxane)
MBM 3-methacryloxypropylbis(trimethylsiloxy)methylsilane
AcPDMS bis-3-methacryloxy-2-hydroxypropyloxypropyl polydimethylsiloxane
Triglide tripropyleneglycol methyl ether
CGI 819 bis(2,4,6-trimethylbenzoyl)-phenylphosphineoxide
PVP low MW poly(N-vinylpyrrolidone) (K value 12)

Throughout the Examples intensity is measured using an IL 1400A radiometer, using an XRL 140A sensor.

Examples 1-10

The reaction components and diluent (D30) listed in Table 1 were mixed together with stirring or rolling for at least about 3 hours at about 23° C., until all components were dissolved. The reactive components are reported as weight percent of all reactive components and the diluent is weight percent of final reaction mixture. The reaction mixture was placed into thermoplastic contact lens molds (made from Topas® copolymers of ethylene and norbornene obtained from Ticona Polymers), and irradiated using Philips TL 20W/03T fluorescent bulbs at 45° C. for about 20 minutes in $N_2$. The molds were opened and lenses were extracted into a 50:50 (wt) solution of IPA and $H_2O$, and soaked in IPA at ambient temperature for about 15 hours to remove residual diluent and monomers, placed into deionized $H_2O$ for about 30 minutes, then equilibrated in borate buffered saline for at least about 24 hours and autoclaved at 122° C. for 30 minutes. The properties of the resulting lenses are shown in Table 1.

Example 11

Lenses having the formulation of Example 1 were remade, without controlling cure intensity. The mechanical properties are reported in Table 2, below. These lenses were clinically evaluated using ACUVUE® 2 lenses as controls. The lenses were worn by 6 patients in a daily wear mode (nightly removal) for a period of one week. At one week the PLTF-NIBUT was 3.6 (±3.0) seconds compared to 5.8 (±2.5) seconds for ACUVUE® 2 lenses. The front surface deposition was graded none to slight for 50% of the test lenses and 100% for the control lenses. The movement was acceptable for both test and control lenses.

TABLE 1

| | EX. # | | | | | | | | | |
|---|---|---|---|---|---|---|---|---|---|---|
| | 1 | 2 | 3 | 4 | 5 | 6 | 7 | 8 | 9 | 10 |
| Comp. | | | | | | | | | | |
| SiGMA | 28 | 30 | 28.6 | 28 | 31 | 32 | 29 | 39.4 | 20 | 68 |
| PVP (K90) | 7 | 10 | 7.1 | 7 | 7 | 7 | 6 | 6.7 | 3 | 7 |
| DMA | 23.5 | 17 | 24.5 | 23.5 | 20 | 20 | 24 | 16.4 | 37 | 22 |
| MPDMS | 31 | 32 | 0 | 31 | 31 | 34 | 31 | 29.8 | 15 | 0 |
| TRIS | 0 | 0 | 0 | 0 | 0 | 0 | 0 | 0 | 15 | 0 |
| HEMA | 6 | 6 | 6.1 | 6 | 6.5 | 3 | 5.5 | 2.9 | 8 | 0 |
| Norbloc | 2 | 2 | 0 | 2.0 | 2 | 2 | 2 | 1.9 | 0 | 0 |
| CGI 1850 | 0.98 | 1 | 1.02 | 1 | 1 | 1 | 1 | 1 | 1 | 0 |
| TEGDMA | 1.5 | 2 | 1.02 | 1.5 | 1.5 | 1 | 1.5 | 1.9 | 0 | 2 |
| TrEGDMA | 0 | 0 | 0 | 0 | 0 | 0 | 0 | 0 | 1 | 0 |
| Blue HEMA | 0.02 | 0 | 0 | 0 | 0 | 0 | 0 | 0 | 0 | 0 |
| mPDMS-OH | 0 | 0 | 31.6 | 0 | 0 | 0 | 0 | 0 | 0 | 0 |
| Darocur 1173 | 0 | 0 | 0 | 0 | 0 | 0 | 0 | 0 | 0 | 1 |
| D30 % | 23 | 26 | 17 | 23 | 23 | 29 | 32 | 28 | 17 | 27 |
| Properties | | | | | | | | | | |
| % EWC[1] | 36 | 33 | 39 | 40 | 36 | 37 | 39 | 25 | 48 | 29 |
| Modulus (psi) | 68 | 78 | 112 | 61 | 67 | 50 | 66 | 92 | 43 | 173 |
| % Elongation | 301 | 250 | 147 | 294 | 281 | 308 | 245 | 258 | 364 | 283 |
| DCA[2] (advancing) | 62 | 55 | 58 | 64 | 72 | 65 | 61 | 55 | 92 | 72 |
| Dk[3] (edge corrected) | 103 | 111 | 101 | 131 | 110 | 132 | 106 | 140 | 64 | 76 |

[1]Equilibrium water content
[2]Dynamic contact angle, measured with physiological borate-buffered saline using a Wilhelmy balance.
[3]Oxygen permeability, edge corrected, in Barrers.

The results of Examples 1-10 show that the reaction mixture components and their amounts may be varied substantially, while still providing uncoated lenses having an excellent balance of mechanical properties and wettability. The contact angle (DCA) of Example 9 may be too high to form a lens that would be clinically wettable, and the modulus may be lower than desired to provide a mechanically robust lens. Example 9 contained the lowest concentration of SiGMA (20%). Because the SiGMA had been reduced, less PVP could be added to the formulation and still provide a compatible reaction mixture. Thus, these examples show that SiGMA is effective in compatibilizing PVP and that when sufficient SiGMA and PVP are present lenses with desirable wettability and other mechanical properties can be made without any form of surface modification.

Example 12

Example 11 was repeated except that the cure intensity was reduced to 1.0 mW/cm². The mechanical properties are reported in Table 2, below. These lenses were clinically evaluated using ACUVUE® 2 lenses as controls. The test lenses were worn by 15 patients in a daily wear mode (nightly removal), in one eye for a period of one week and an ACUVUE® 2 lens was worn in the contralateral eye. At one week the PLTF-NIBUT was 8.2 (±1.7) seconds compared to 6.9 (±1.5) seconds for ACUVUE® 2 lenses. The front surface deposition was graded none to slight for all of the patients for both test and control lenses. The movement was acceptable for both test and control lenses.

TABLE 2

|  | Ex. # | | |
|---|---|---|---|
|  | 1 | 11 | 12 |
| % EWC | 36 | 36 | 36 |
| Modulus (psi) | 68 | 74 | 87 |
| Elongation | 301 | 315 | 223 |
| DCA | 62 | 77 | 56 |
| Dk | 103 | 127 | 102 |

Generally the mechanical properties for Examples 1, 11 and 12 are consistent results for multiple runs of the same material. However, the clinical results for Examples 11 (uncontrolled cure intensity) and 12 (low, controlled cure intensity) are substantially different. The on eye wettability after one week of wear for Example 11 (measured by PLTF-NIBUT) was worse that the ACUVUE® 2 lenses (3.6 v. 5.8) and half the lenses had more than slight surface depositions. The Example 12 lenses (controlled, low intensity cure) displayed significantly improved on-eye wettability, which was measurably better than ACUVUE® 2 lenses (8.2 v. 6.9) and no surface depositions. Thus, using a low, controlled cure provides an uncoated lens having on-eye wettability which is as good as, and in some cases better than conventional hydrogel lenses.

Examples 13-17

Reaction mixtures described in Table 3 and containing low or no hydroxyl-functionalized silicone containing monomer (in these Examples SiGMA) were mixed with constant stirring at room temperature for 16 hours. Even after 16 hours each of the reaction mixtures remained cloudy and some contained precipitates. Accordingly, these reaction mixtures could not be used to produce lenses.

TABLE 3

|  | Ex. # | | | | |
|---|---|---|---|---|---|
| Composition | 13 | 14 | 15 | 16 | 17 |
| SiGMA | 0 | 0 | 0 | 10 | 20 |
| PVP (K90) | 12 | 12 | 10 | 8.0 | 8.0 |
| DMA | 10 | 10 | 8.3 | 19 | 19 |
| MPDMS | 37 | 37 | 30.8 | 35 | 28 |
| TRIS | 14 | 14 | 11.7 | 17 | 14 |
| HEMA | 25 | 25 | 37.5 | 8.0 | 8.0 |
| TEGDMA | 1.0 | 1.0 | 0.83 | 2.0 | 2.0 |
| Darocur 1173 | 1.0 | 1.0 | 0.83 | 1.0 | 1.0 |

TABLE 3-continued

|  | Ex. # | | | | |
|---|---|---|---|---|---|
| Composition | 13 | 14 | 15 | 16 | 17 |
| D30 % | 23 | 31 | 31 | 27 | 27 |

Examples 13 through 15 show that reaction mixtures without any hydroxyl-functionalized silicone containing monomer (SiGMA or mPDMS-OH) are incompatible, and not suitable for making contact lenses. Examples 16 and 17 show that concentrations of hydroxyl-functionalized silicone containing monomer less than about 20 weight % are insufficient to compatibilize significant amounts of high molecular weight PVP. However, comparing Example 17 to Example 9, lesser amounts of high molecular weight PVP (3 weight %) can be included and still form a compatible reaction mixture.

Examples 18-25

A solution of 1.00 gram of D3O, 1.00 gram of mPDMS and 1.00 gram of TRIS was placed in a glass vial (Ex. 19). As the blend was rapidly stirred at about 20 to 23° C. with a magnetic stir bar, a solution of 12 parts (wt) PVP (K90) and 60 parts DMA was added dropwise until the solution remained cloudy after 3 minutes of stirring. The mass of the added DMA/PVP blend was determined in grams and reported as the "monomer compatibility index". This test was repeated using SiGMA (Ex. 18), MBM (Ex. 20), MPD (Ex. 21), acPDMS, where n=10 (Ex. 22), acPDMS where n=20 (Ex. 23), iSiGMA-3Me (Ex. 24) and TRIS2-HOEOP2 (Ex. 25) as test silicone monomers in place of TRIS.

TABLE 4

| Ex. # | Test silicone-containing monomer | Monomer compatibility index | Si:OH |
|---|---|---|---|
| 18 | SiGMA | 1.8 | 3:1 |
| 19 | TRIS | 0.07 | 4:0 |
| 20 | MBM | 0.09 | 3:0 |
| 21 | MPD | 0.05 | 2:0 |
| 22 | acPDMS (n = 10)* | 1.9 | 11:2 |
| 23 | acPDMS (n = 20)* | 1 | 21:2 |
| 24 | ISiMAA-3Me | 0.15 | 4:0 |
| 25 | TRIS2-HOEOP2 | 0.11 | 3:2 |
| 26 | MPDMS-OH | 0.64 | ~11:1 |

Structures for acPDMS, iSiGMA-3Me and TRIS2-HOEOP2 are shown below.

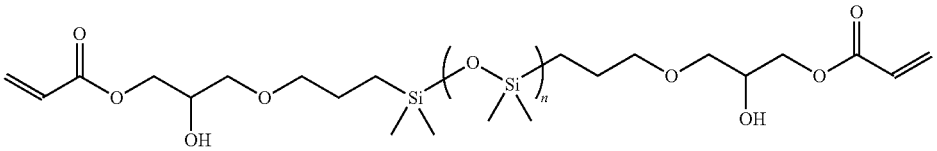

acPDMS (n averages 10 or 20):

TRIS2-HOEOP2

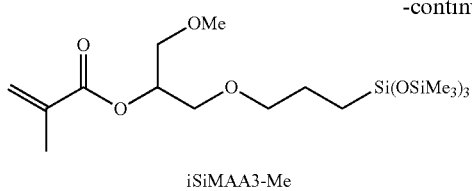

iSiMAA3-Me

The results, shown in Table 4, show that SiGMA, acPDMS (where n=10 and 20) and mPDMS-OH more readily incorporate into a blend of a diluent, another silicone containing monomer, a hydrophilic monomer, and an high molecular weight polymer (PVP) than alternative silicone-containing monomers. Thus, compatibilizing silicone containing monomers having a compatibility index of greater than about 0.5 are useful for compatibilizing high molecular weight hydrophilic polymers like PVP.

Example 27-35

Lenses were made using the reaction mixture formulation of Example 1. The plastic contact lens molds (made from Topas® copolymers of ethylene and norbornene obtained from Ticona Polymers) were stored overnight in nitrogen (<0.5% $O_2$) before use. Each mold was dosed with 75 μl reaction mixture. Molds were closed and lenses photocured using the times and cure intensities indicated in Table 5. Lenses were formed by irradiation of the monomer mix using visible light fluorescent bulbs, curing at 45° C. The intensity was varied by using a variable balast or light filters, in two steps of varied intensity and cure time. The step 2 time was selected to provide the same total irradiation energy (about 830 $mJ/cm^2$) for each sample.

The finished lenses were demolded using a 60:40 mixture of IPA/water. The lenses were transferred to a jar containing 300 g 100% isopropyl alcohol (IPA). The IPA was replaced every 2 hours for 10 hours. At the end of about 10 hours, 50% of the IPA was removed and replaced with DI water and the jar was rolled for 20 minutes After 20 minutes, 50% of the IPA was removed and replaced with DI water and the jar was rolled for another 20 minutes. The lenses were transferred to packing solution, rolled for 20 minutes and then tested.

TABLE 5

| Ex. # | Step 1 intensity ($mW/cm^2$) | Step 1 time (min:sec) | Step 2 intensity ($mW/cm^2$) | Step 2 time (min:sec) | Advancing Contact Angle |
|---|---|---|---|---|---|
| 27 | 1.1 | 6:55 | 5.5 | 1:28 | 51 ± 1 |
| 28 | 1.1 | 2:46 | 5.5 | 2:21 | 55 ± 2 |
| 29 | 1.1 | 11:03 | 5.5 | 0:35 | 55 ± 1 |
| 30 | 1.7 | 6:30 | 5.5 | 0:35 | 50 ± 1 |
| 31 | 1.7 | 1:37 | 5.5 | 2:21 | 55 ± 1 |
| 32 | 1.7 | 4:04 | 5.5 | 1:28 | 54 ± 2 |
| 33 | 2.4 | 2:52 | 5.5 | 1:28 | 62 ± 6 |
| 34 | 2.4 | 4:36 | 5.5 | 0:35 | 76 ± 9 |
| 35 | 2.4 | 1:09 | 5.5 | 0:35 | 78 ± 6 |

The contact angles for Examples 27 through 32 are not significantly different, indicating that step 1 cure intensities of less than about 2 $mW/cm^2$ provide improved wettability for this lens formulation regardless of the step 1 cure time. However, those of skill in the art will appreciate that shorter step 1 cure times (such as those used in Examples 28 and 31) allow for shorter overall cure cycles. Moreover, it should be noted that even though the contact angles for Examples 33 through 35 are measurably higher than those of Examples 27-32, the lenses of Examples 33-35 may still provide desirable on eye wettability.

Examples 36-41

The reaction components of Example 1, were blended with either 25% or 40% D30 as diluent in accordance with the procedure of Example 1. The resultant reaction mixtures were charged into plastic contact lens molds (made from Topas® copolymers of ethylene and norbornene obtained from Ticona Polymers) and cured in a glove box under a nitrogen atmosphere, at about 2.5 $mW/cm^2$ intensity, about 30 minutes and the temperatures shown in Table 6, below. The lenses were removed from the molds, hydrated and autoclaved as describe in Example 1. After hydration the haze values of the lenses were determined. The results shown in Table 6 show that the degree of haziness was reduced at the higher temperatures. The results also show that as the concentration of diluent decreases the haze also decreases.

TABLE 6

| Ex. # | % D30 | Temp. (° C.) | % haze | DCA(°) |
|---|---|---|---|---|
| 36 | 25 | 25 | 30 (6) | 99 |
| 37 | 25 | 50-55 | 12 (2) | 100 |
| 38 | 25 | 60-65 | 14 (0.2) | 59 |
| 39 | 40 | 25 | 50 (10) | 68 |
| 40 | 40 | 50-55 | 40 (9) | 72 |
| 41 | 40 | 60-65 | 32 (1) | 66 |

*Haze (std. dev.)

The results in Table 6 show that haze may be reduced by about 20% (Example 41 v. Example 39) and up to as much as about 65% (Example 37 v. Example 36) by increasing the cure temperature. Decreasing diluent concentration from 40 to 25% decrease haze by between about 40 and 75%.

Examples 42-47

Lenses were made from the formulations shown in Table 7 using the procedure of Example 1, with a 30 minute cure time at 25° C. and an intensity of about 2.5 $mW/cm^2$. Percent haze was measured and is reported in Table 8.

TABLE 7

| | Ex. # | | | | | |
|---|---|---|---|---|---|---|
| | 42 | 43 | 44 | 45 | 46 | 47 |
| SiGMA | 28.0 | 28.0 | 28.0 | 28.0 | 28.0 | 28.0 |
| mPDMS | 31.0 | 31.0 | 28.0 | 28.0 | 28.0 | 28.0 |
| acPDMS (n = 10) | 0.0 | 0.0 | 4.0 | 4.0 | 4.0 | 4.0 |
| DMA | 23.5 | 23.5 | 23.5 | 23.5 | 24.0 | 24.0 |
| HEMA | 6.0 | 6.0 | 5.0 | 5.0 | 6.0 | 6.0 |
| TEGDMA | 1.5 | 1.5 | 1.5 | 1.5 | 0.0 | 0.0 |
| Norbloc | 2.0 | 2.0 | 2.0 | 2.0 | 2.0 | 2.0 |
| PVP (K-90) | 7.0 | 7.0 | 7.0 | 7.0 | 7.0 | 7.0 |
| CGI 1850 | 1.0 | 1.0 | 1.0 | 1.0 | 1.0 | 1.0 |
| D30 | 25.0 | 40 | 25.0 | 40.0 | 25.0 | 40.0 |

TABLE 7-continued

| | Ex. # | | | | | |
|---|---|---|---|---|---|---|
| | 42 | 43 | 44 | 45 | 46 | 47 |
| Properties | | | | | | |
| Haze | 30 | 50 | 7.3 | 14 | 26 | 25 |
| Modulus (psi) | 74 | 56 | 148 | 104 | 74 | NT |
| Elongation (%) | 326 | 395 | 188 | 251 | 312 | NT |
| EWC (%) | 38 | 41 | 33 | 35 | 38 | 39 |

A comparison of the results for formulations having the same amount of diluent and either TEGDMA or acPDMS (Examples 42 and 46 and Examples 43 and 47) shows that acPDMS is an effective crosslinker and provides lenses with properties which are comparable to those where TEGDMA is used as a crosslinker. Examples 44 and 45 contain both crosslinkers. Haze for these Examples decreased substantially compared to the lenses made from either crosslinker alone. However, modulus and elongation were negatively impacted (likely because the amount of crosslinker was too great).

Examples 48-54

Reaction mixtures were made using the formulations shown in Table 8 with the diluents indicated. The reaction mixtures were placed into thermoplastic contact lens molds, and irradiated using Philips TL 20W/03T fluorescent bulbs at 45° C., 0.8 mW/cm² for about 32 minutes. The molds were opened and lenses were released into deionized water at 95° C. over a period of 20 minutes. The lenses were then placed into borate buffered saline solution for 60 minutes and autoclaved at 122° C. and 30 minutes. The properties of the resulting lenses are shown in Table 9.

TABLE 8

| | Ex. # | | | | | | |
|---|---|---|---|---|---|---|---|
| | 48 | 49 | 50 | 51 | 52 | 53 | 54 |
| Components | | | | | | | |
| SiGMA | 30 | 30 | 30 | 33 | 34 | 25 | 20 |
| PVP | 6 | 6 | 6 | 6 | 7 | 6 | 6 |
| DMA | 31 | 31 | 31 | 30 | 30 | 31 | 31 |
| MPDMS | 19 | 22 | 23.5 | 16.5 | 19 | 25 | 28 |
| AcPDMS (n = 10) | 2 | 0 | 0 | 3 | 0 | 0 | 0 |
| HEMA | 9.85 | 8.5 | 6.95 | 9 | 6 | 10.5 | 12.5 |
| Norbloc | 1.5 | 1.5 | 1.5 | 2 | 1.5 | 1.5 | 1.5 |
| CGI 819 | 0.23 | 0.23 | 0.25 | 0.48 | 0 | 0.23 | 0.23 |
| CGI 1850 | 0 | 0 | 0 | 0 | 1 | 0 | 0 |
| EGDMA | 0.4 | 0.75 | 0.8 | 0 | 0 | 0.75 | 0.75 |
| TEGDMA | 0 | 0 | 0 | 0 | 1.5 | 0 | 0 |
| Blue HEMA | 0.02 | 0.02 | 0 | 0 | 0 | 0.02 | 0.02 |
| % Diluent* | 40 | 40 | 27.3 | 39.4 | 25.9 | 40 | 40 |
| Diluent comp | A | A | B | C | D | A | A |
| Properties | | | | | | | |
| EWC (%) | 45 | 45 | 47 | 49 | 47 | 49 | 50 |
| DCA (advancing) | 52 (2) | 51 (7) | 74 (10) | 108 | 75 (6) | 47(2) | 56 (11) |
| Modulus (psi) | 91 | 77 | 69 | 55 | 49 | 63 | 67 |
| Elongation (%) | NT | 232 | 167 | 275 | 254 | 110 | 124 |
| Dk (barrers) | 54 | 60 | 78 | 44 | 87 | 59 | 60 |

Diluents (weight parts):
A = 72.5% t-amyl alcohol and 27.5 PVP ($M_W$ = 2500)
B = t-amyl alcohol
C = 15/38/38% TMP/2M2P/PVP ($M_W$ = 2500)
D = 57/43 2M2P/TMP
NT - not tested Thus, Examples 48 and 51 show that formulations comprising both hydrophilic (EGDMA or TEGDMA) and hydrophobic crosslinkers (acPDMS) provide silicone hydrogel compositions which display an excellent balance of properties including good water content, moderate Dk, wettability, modulus and elongation.

Example 55

The lenses of Example 48 were clinically evaluated. The lenses were worn by 18 patients in a daily wear mode (nightly removal) for a period of one week. At one week the PLTF-NIBUT was 8.4 (±2.9) seconds compared to 7.0 (±1.3) seconds for ACUVUE® 2 lenses. The front surface discrete deposition was graded none to slight for 97% of the patients with the test lenses, compared with 89% in control lenses. The movement was acceptable for both test and control lenses.

Example 56

The lenses of Example 49 were clinically evaluated. The lenses were worn by 18 patients in a daily wear mode (nightly removal) for a period of one week. At one week the PLTF-NIBUT was 8.4 (±2.9) seconds compared to 7 (±1.3) seconds for ACUVUE® 2 lenses. The front surface discrete deposition was graded none to slight for 95% of the patients with the test lenses, compared with 89% in control lenses. The movement was acceptable for both test and control lenses.

Example 57

The lenses of Example 51 were clinically evaluated. The lenses were worn by 13 patients in a daily wear mode (nightly removal) for a period of one week. At one week the PLTF-NIBUT was 4.3 (±1.9) seconds compared to 9.6 (±2.1) seconds for ACUVUE® 2 lenses. The front surface discrete deposition was graded none to slight for 70% of the patients with the test lenses, compared with 92% in control lenses. The movement was acceptable for both test and control lenses. Thus, there is some correlation between contact angle measurements (108° for Example 51 versus 52° for Example 48) and clinical wettability as measure by PLTF-NIBUT (4.3 seconds for Example 51 versus 8.4 seconds for Example 48).

Examples 58-60

Silicone hydrogel lenses were made using the components (expressed in weight parts) listed in Table 9 and the following procedure:

The components were mixed together in a jar to for a reaction mixture. The jar containing the reaction mixture was placed on a jar mill roller and rolled overnight.

The reaction mixture was placed in a vacuum desiccator and the oxygen removed by applying vacuum for 40 minutes. The desiccator was back filled with nitrogen. Contact lenses were formed by adding approximately 0.10 g of the degassed lens material to the concave front curve side of TOPAS® (copolymers of ethylene and norbornene obtained from Ticona Polymers) mold cavities in a glove box with nitrogen purge. The molds were closed with polypropylene convex base curve mold halves. Polymerization was carried out under a nitrogen purge and was photoinitiated with 5 mW cm² of visible light generated using 20W fluorescent lights with a TL-03 phosphor. After curing for 25 minutes at 45° C., the molds were opened. The concave front curve portion of the lens mold was placed into a sonication bath (Aquasonic model 75D) containing deionized water under the conditions (temperature and amount of Tween) shown in Table 10. The lens deblock time is shown in Table 10. The lenses were clear and of the proper shape to be contact lenses.

TABLE 9

|  | Ex. 58 | Ex. 59 | Ex. 60 | Ex. 61 |
| --- | --- | --- | --- | --- |
| SiGMA | 3.05 | 3.2 | 3.2 | 3.0 |
| mPDMS | 1.7 | 1.7 | 1.7 | 1.7 |
| DMA | 3.2 | 3.0 | 3.1 | 3.2 |

TABLE 9-continued

|  | Ex. 58 | Ex. 59 | Ex. 60 | Ex. 61 |
| --- | --- | --- | --- | --- |
| PVP | 0.6 | 0.6 | 0.6 | 0.6 |
| HEMA | 1.0 | 0.8 | 0.8 | 1.0 |
| TEGDMA | 0.2 | 0.4 | 0.3 | 0.2 |
| Norblock | 0.15 | 0.2 | 0.2 | 0.2 |
| CGI 1850 | 0.1 | 0.1 | 0.3 | 0.3 |
| Triglide | 1.5 | 1.5 |  | 1.5 |
| 2M2P | 2.5 | 2.5 | 2.5 | 2.5 |
| PVP low MW | 0.5 | 1.5 | 1.5 | 0.5 |

TABLE 10

| Ex. # | Form. Ex. # | [Tween] (ppm) | Temp (° C.) | Deblock time (min.) |
| --- | --- | --- | --- | --- |
| 62 | 58 | 850 | 75 | 10 |
| 63 | 58 | 10,000 | 70 | 10-15 |
| 64 | 58 | 0 | 75 | 20-22 |
| 65 | 58 | 850 | 22 | 10-15 |
| 66 | 59 | 850 | 85 | 3 |
| 67 | 60 | 850 | 85 | 6 |
| 68 | 61 | 850 | 75 | 18 |

Example 69

The lenses of Example 59 which were deblocked in Example 66, were further hydrated in deionized water at 65° C. for 20 minutes. The lenses were then transferred into borate buffered saline solution and allowed to equilibrate for at least about 24 hours. The lenses were clear and of the proper shape to be contact lenses. The lenses had a water content of 43%, a modulus of 87 psi, an elongation of 175%, and a Dk of 61 barriers. The lenses were found to have an advancing contact angle of 57 degrees. This indicates the lens surfaces were substantially free of leachable hydrophobic material.

Example 70

The concave front curve portion of the lens mold from Example 61 was placed into a sonication bath (Aquasonic model 75D) containing about 5% DOE-120 in deionized water at about 75° C. The lenses deblocked from the frame in 18 minutes.

Example 71 (Use of an Organic Solvent)

The concave front curve portion of the lens mold from example 61 was placed into a sonication bath (Aquasonic 75D) containing about 10% of 2-propanol in deionized water at 75° C. The lenses deblocked form the frame in 15 minutes. When Tween was used as the additive (Example 68) the deblock time was 18 minutes. Thus, the present example shows that organic solvents may also be used to deblock lenses comprising low molecular weight hydrophilic polymers.

Example 72 (Contains No Low Molecular Weight PVP)

Silicone hydrogel lenses wee made using the formulation and procedure of Example 58, but without any low molecular weight PVP. The following procedure was used to deblock the lenses.

The concave front curve portion of the lens mold was placed into a sonication bath (Aquasonic model 75D) containing about 850 ppm of Tween in deionized water at about 65° C. The lenses did not release from the mold. The deblock time for the formulation which contained low molecular weight hydrophilic polymer (Example 58 formulation) under similar deblock conditions (Example 62-850 ppm Tween and 75° C.) was 10 minutes. Thus, the present Example shows that deblocking cannot be accomplished in water only, in this formulation without including low molecular weight hydrophilic polymer in the formulation.

Example 73

The concave front curve portion of the lens mold from example 72 was placed into a sonication bath (Aquasonic 75D) containing about 10% of 2-propanol an organic solvent in deionized water at 75° C. The lenses deblocked form the frame in 20 to 25 minutes. Thus, lenses of the present invention which do not contain low molecular weight hydrophilic polymer may be deblocked using an aqueous solution comprising an organic solvent.

Examples 74-76

Formulations and lenses were made according to Example 49, but with varying amounts of photoinitiator (0.23, 0.38 or 0.5 wt. %), curing at 45° C. with Philips TL 20W/03T fluorescent bulbs (which closely match the spectral output of the visible light used to measure gel time) irradiating the molds at 2.0 mW/cm$^2$. The advancing contact angles of the resulting lenses are shown in Table 11.

TABLE 11

| Ex. # | Wt % | Advancing DCA | Gel time (sec) |
|---|---|---|---|
| 74 | 0.23 | 59 (4) | 65 |
| 75 | 0.38 | 62 (6) | 57 |
| 76 | 0.5 | 80 (7) | 51 |

Examples 77-79

Gel times were measured for the formulation of Example 1 at 45° C. at 1.0, 2.5 and 5.0 mW/cm$^2$. The results are shown in Table 12.

TABLE 12

| Ex. # | Intensity (mW/cm$^2$) | gel time (sec) |
|---|---|---|
| 77 | 1 | 52 |
| 78 | 2.5 | 38 |
| 79 | 5 | 34 |

The results of Examples 74 through 76 and 77 through 79 compared with Examples 27-35, show that as gel times increase, wettability improves. Thus, gel points can be used, in coordination with contact angle measurements, to determine suitable cure conditions for a given polymer formulation and photoinitiator system.

Examples 79-83

Reaction mixtures were made using reactive components shown in Table 14 and 29% (based upon all reactive components and diluent) t-amyl alcohol as a diluent and 11% PVP 2,500 (based upon reactive components). Amounts indicated are based upon 100% reactive components. The reaction mixtures were placed into thermoplastic contact lens molds, and irradiated using Philips TL 20W/03T fluorescent bulb at 60° C., 0.8 mW/cm$^2$ for about 30 minutes under nitrogen. The molds were opened and lenses were released into deionized water at 95° C. over a period of 15 minutes. The lenses were then placed into borate buffered saline solution for 60 minutes and autoclaved at 122° C. for 30 min. The properties of the resulting lenses are shown in Table 13.

TABLE 13

| | Ex. # | | | | |
|---|---|---|---|---|---|
| | 79 | 80 | 81 | 82 | 83 |
| Components | | | | | |
| SiGMA | 30 | 30 | 30 | 30 | 30 |
| PVP | 0 | 1 | 3 | 6 | 8 |
| DMA | 37 | 36 | 34 | 31 | 29 |
| MPDMS | 22 | 22 | 22 | 22 | 22 |
| HEMA | 8.5 | 8.5 | 8.5 | 8.5 | 8.5 |
| Norbloc | 1.5 | 1.5 | 1.5 | 1.5 | 1.5 |
| CGI 819 | 0.25 | 0.25 | 0.25 | 0.25 | 0.25 |
| EGDMA | 0.75 | 0.75 | 0.75 | 0.75 | 0.75 |
| Properties | | | | | |
| DCA (advancing) | 122(8) | 112(6) | 66(13) | 58(8) | 54(3) |
| Haze | 18(4) | 11(1) | 13(1) | 14(2) | 12(1) |

Table 12 shows that the addition of PVP dramatically decreases contact angle. As little as 1% decreases the dynamic contact angle by about 10% and as little as 3% decreases dynamic contact angle by about 50%.

Examples 84-86

Silicone hydrogel lenses were made using the components listed in Table 14 and the following procedure:

The reactive components and diluent were mixed together at room temperature in a jar. The jar containing the reaction mixture was placed on a jar mill roller and rolled overnight.

The reaction mixture was placed in a vacuum desiccator and the oxygen removed by applying vacuum for 40 minutes. The desiccator was back filled with nitrogen. Contact lenses were formed by adding approximately 0.10 g of the degassed lens material to the concave front curve side of TOPAS® mold cavities in a glove box with nitrogen purge. The molds were closed with polypropylene convex base curve mold halves. Polymerization was carried out under a nitrogen purge and was photoinitiated with 1.0 mW cm$^2$ of visible light generated using 20W fluorescent lights with a TL-03 phosphor. After curing for 15 minutes at 45° C., the molds were opened. The concave front curve portion of the lens mold was placed into de-ionized water at 95-100° C. The lens deblock time is shown in Table 14. The lenses were clear and of the proper shape to be contact lenses.

TABLE 14

| | Ex. # | | |
|---|---|---|---|
| Components | 84 | 85 | 86 |
| SiGMA | 30 | 30 | 30 |
| PVP | 6 | 6 | 6 |
| DMA | 31 | 31 | 31 |

TABLE 14-continued

| Components | Ex. # 84 | Ex. # 85 | Ex. # 86 |
|---|---|---|---|
| MPDMS | 21 | 21 | 21 |
| AcPDMS (n = 10) | 0 | 0 | 0 |
| HEMA | 9.25 | 9.25 | 9.25 |
| Norbloc | 1.5 | 1.5 | 1.5 |
| CGI 819 | 0.25 | 0.25 | 0.25 |
| CGI 1850 | 0 | 0 | 0 |
| EGDMA | 1.0 | 1.0 | 1.0 |
| TEGDMA | 0 | 0 | 0 |
| Blue HEMA | 0 | 0 | 0 |
| % Diluent* | 40.0 | 40.0 | 40.0 |
| Diluent comp | E | F | G |
| DCA (advancing) | 53(3) | 55(3) | 56(9) |
| Haze | 15(3) | 22(2) | 16(2) |
| Deblock Time (min) | 3 | 5 | 8 |

Diluents (weight parts of diluent):
E = 62.5% t-amyl alcohol and 37.5% PVP ($M_W$ = 2500)
F = 62.5% t-amyl alcohol and 37.5% 1,3-dimethyl-3,4,5,6-tetrahydro-2(1H)-pyrimidinone
G = 62.5% t-amyl alcohol and 37.5% ethyl-4-oxo-1-piperidinecarboxylate Thus, Examples 84-86 show that a variety of release agents are useful for improving deblocking.

Example 87

A reaction mixture was made using reactive components shown in Table 15 and 42% (based upon all reactive components and diluent) t-amyl alcohol as a diluent. The reaction mixtures were placed into thermoplastic contact lens molds, and irradiated using Philips TL 20W/03T fluorescent bulb at 50° C., 0.8 mW/cm² for about 30 minutes under nitrogen. The molds were opened and lenses were released into deionized water at room temperature over a period of 15 minutes. The lenses were then placed into borate buffered saline solution for 60 minutes and autoclaved at 122° C. for 30 min. The properties of the resulting lenses are shown in Table 12.

TABLE 12

| Components | Ex. # 87 |
|---|---|
| SiGMA | 0 |
| PVP | 7 |
| DMA | 25 |
| MPDMS | 48.6 |
| AcPDMS | 5 |
| HEMA | 12.25 |
| Norbloc | 1.5 |
| CGI 819 | 0.25 |
| TEGDMA | 0.4 |

Example 88

Preparation of mPDMS-OH (Used in Examples 3)
96 g of Gelest MCR-E11 (mono-(2,3-epoxypropyl)-propyl ether terminated polydimethylsiloxane (1000 MW)), 11.6 g methacrylic acid, 0.10 g triethylamine and 0.02 g hydroquinone monomethylether were combined and heated to 140° C. with an air bubbler and with stirring for 2.5 hours. The product was extracted with saturated aqueous NaHCO₃ and CH₂Cl₂. The CH₂Cl₂ layer was dried over Na₂SO₄ and evaporated to give 94 g of product. HPLC/MS was consistent with desired structure:

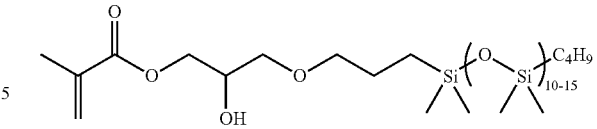

What is claimed is:

1. A method for improving the wettability of an ophthalmic device formed from a reaction mixture comprising adding at least one high molecular weight hydrophilic polymer and an effective amount of at least one compatibilizing monomer to said reaction mixture, and curing said reaction mixture, wherein said reaction mixture is free from silicone containing macromers having hydroxyl functionality and comprises in addition to said at least one high molecular weight hydrophilic polymer and at least one compatibilizing monomer
    (a) about 10 to about 50 wt % at least one hydrophilic monomer selected from the group consisting of N,N-dimethylacrylamide (DMA), 2-hydroxyethyl methacrylate (HEMA), glycerol methacrylate, 2-hydroxyethyl methacrylamide, N-vinylpyrrolidone (NVP), polyethyleneglycol monomethacrylate, methacrylic acid, acrylic acid and combinations thereof; and
    (b) about 10 to about 50 wt % at least one monomethacryloxypropyl terminated polydimethylsiloxanes.
2. The method of claim 1 wherein said compatibilizing monomer has a compatibility index of greater than about 0.5.
3. The method of claim 1 wherein said compatibilizing monomer has a compatibility index of greater than about 1.
4. The method of claim 1 wherein said compatibilizing monomer comprises at least one siloxane group.
5. The method of claim 4 wherein said compatibilizing monomer has a Si to OH ratio of less than about 15:1.
6. The method of claim 4 wherein said compatibilizing monomer has a Si to OH ratio of between about 1:1 to about 10:1.
7. The method of claim 1 wherein said hydrophilic polymer is selected from the group consisting of poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, and poly-N-vinyl-4,5-dimethyl-2-pyrrolidone, polyvinylimidazole, poly-N—N-dimethylacrylamide, polyvinyl alcohol, polyacrylic acid, polyethylene oxide, poly 2 ethyl oxazoline, heparin polysaccharides, polysaccharides, mixtures and copolymers thereof.
8. The method of claim 1 wherein said hydrophilic polymer comprises poly-N-vinylpyrrolidone.
9. The method of claim 1 comprising about 1 to about 15 weight % high molecular weight hydrophilic polymer.
10. The method of claim 1 comprising about 3 to about 15 weight % high molecular weight hydrophilic polymer.
11. The method of claim 1 comprising about 5 to about 12 weight % high molecular weight hydrophilic polymer.
12. The method of claim 1 wherein said compatibilizing components comprises at least one hydroxyl-functionalized silicone-containing monomer is a compound of Formula I or II

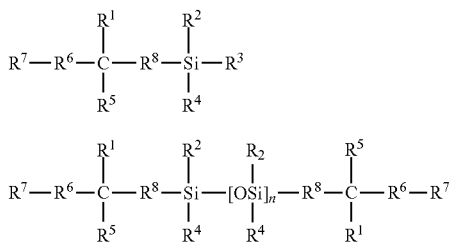

wherein:

n is an integer between 3 and 35

$R^1$ is hydrogen, $C_{1-6}$ alkyl, $R^2$, $R^3$, and $R^4$, are independently, $C_{1-6}$ alkyl, tri$C_{1-6}$ alkylsiloxy, phenyl, naphthyl, substituted $C_{1-6}$ alkyl, substituted phenyl, or substituted naphthyl where the alkyl substitutents are selected from one or more members of the group consisting of $C_{1-6}$ alkoxycarbonyl, $C_{1-6}$ alkyl, $C_{1-6}$ alkoxy, amide, halogen, hydroxyl, carboxyl, $C_{1-6}$ alkylcarbonyl and formyl, and where the aromatic substitutents are selected from one or more members of the group consisting of $C_{1-6}$ alkoxycarbonyl, $C_{1-6}$ alkyl, $C_{1-6}$ alkoxy, amide, halogen, hydroxyl, carboxyl, $C_{1-6}$ alkylcarbonyl and formyl;

$R^5$ is a hydroxyl, an alkyl group containing one or more hydroxyl groups, or $(CH_2(CR^9R^{10})_yO)_x)$—$R^{11}$ wherein y is 1 to 5, preferably 1 to 3, x is an integer of 1 to 100, preferably 2 to 90 and more preferably 10 to 25; $R^9$-$R^{11}$ are independently selected from H, alkyl having up to 10 carbon atoms and alkyls having up to 10 carbon atoms substituted with at least one polar functional group;

$R^6$ is a divalent group comprising up to 20 carbon atoms;

$R^7$ is a monovalent group that can undergo free radical or cationic polymerization, comprising up to 20 carbon atoms, and R8 is a divalent or trivalent group comprising up to 20 carbon atoms.

13. The method of claim 12 wherein the effective amount of hydroxyl-functionalized silicone-containing monomer is about 20% to about 50%.

14. The method of claim 12 wherein said hydroxyl-functionalized silicone-containing monomer is selected from the group consisting of 2-propenoic acid, 2-methyl-2-hydroxy-3-[3-[1,3,3,3-tetramethyl-1-[trimethylsilyl)oxy]disiloxanyl]propoxy]propyl ester, (3-methacryloxy-2-hydroxypropyloxy)propyltris(trimethylsiloxy)silane, (2-methacryloxy-3-hydroxypropyloxy)propylbis(trimethylsiloxy)methylsilane and mixtures thereof.

15. The method of claim 1 wherein said at least one monomethacryloxypropyl terminated polydimethylsiloxane is present in an amount of about 10 to about 40%.

16. The method of claim 1 wherein said at least one hydrophilic monomer comprises N,N-dimethylacrylamide.

17. The method of claim 12 comprising about 5 to about 12 weight % high molecular weight hydrophilic polymer and about 20 to about 50 weight % hydroxyl-functionalized silicone-containing monomer.

18. The method of claim 1 wherein said hydrophilic polymer has a weight average molecular weight of at least about 10,000 daltons.

19. The method of claim 1 wherein said hydrophilic polymer comprises at least one cyclic moiety along a backbone portion of said hydrophilic polymer.

20. The method of claim 1 wherein said hydrophilic polymer is selected from the group consisting of polymers comprising cyclic amides, cyclic imides and combinations thereof.

21. The method of claim 1 wherein said ophthalmic device comprises an advancing dynamic contact angle of less than about 70°.

22. The method of claim 1 wherein said ophthalmic device comprises an advancing dynamic contact angle of less than about 60°.

23. The method of claim 1 wherein said ophthalmic device comprises, after about one day of wear, a tear film break up time of at least about 7 seconds and an oxygen permeability of at least about 50 barrers.

24. The method of claim 1 wherein said ophthalmic device comprises a modulus of less than about 90 psi.

25. The method of claim 1 wherein said ophthalmic device comprises a water content between about 10 and about 60%.

26. The method of claim 1 wherein said ophthalmic device comprises a water content between about 20 and about 55%.

27. The method of claim 1 wherein said ophthalmic device comprises a water content between about 25 and about 40%.

28. The method of claim 23 wherein said tear film breakup time is at least about 7 seconds after about 7 days of wear.

29. The method of claim 1 wherein said reaction mixture further comprises at least one initiator.

30. The method of claim 29 wherein said curing is conducted via heat, exposure to radiation or a combination thereof.

31. The method of claim 29 wherein said curing is conducted via irradiation comprises ionizing and/or actinic radiation and said initiator comprises at least one photoinitiator.

32. The method of claim 31 wherein said radiation comprises light having a wavelength of about 200 to about 500 nm and said initiator is selected from the group consisting of aromatic alpha-hydroxy ketones, alkoxyoxybenzoins, acetophenones, acyl phosphine oxides, mixtures of tertiary amines and diketones, and mixtures thereof.

33. The method of claim 31 wherein said reaction mixture further comprise initiator is selected from the group consisting of 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide, bis(2,4,6-trimethylbenzoyl)-phenylphosphineoxide, 2,4,6-trimethylbenzyldiphenyl phosphine oxide and 2,4,6-trimethylbenzyoyl diphenylphosphine oxide, benzoin methyl ester, combinations of camphorquinone and ethyl 4-(N,N-dimethylamino)benzoate and mixtures thereof.

34. The method of claim 29 wherein said initiator is present in the reaction mixture in amounts effective to initiate polymerization of the reaction mixture.

35. The method of claim 29 wherein said initiator is present in the reaction mixture in amounts from about 0.1 to about 2 weight percent based upon said reactive components.

36. The method of claim 31 wherein said curing is conducted via visible light irradiation.

37. The method of claim 33 wherein said initiator comprises 1-hydroxycyclohexyl phenyl ketone, bis(2,6-dimethoxybenzoyl)-2,4-4-trimethylpentyl phosphine oxide and mixtures thereof.

38. The method of claim 33 wherein said initiator comprises bis(2,4,6-trimethylbenzoyl)-phenylphosphineoxide.

39. The method of claim 1 wherein said reactive components further comprises at least one UV absorbing compound.

40. The method of claim 36 wherein said curing step is conducted at a cure intensity between about 0.1 and about 6 mW/cm$^2$.

41. The method of claim 36 wherein said curing step is conducted at a cure intensity of between about 0.2 mW/cm$^2$ to about 3 mW/cm$^2$.

42. The method of claim 40 wherein said curing step further comprises a cure time of at least about 1 minute.

43. The method of claim 40 wherein said curing step further comprises a cure time of between about 1 and about 60 minutes.

44. The method of claim 40 wherein said curing step further comprises a cure time of between about 1 and about 30 minutes.

45. The method of claim 42 wherein said curing step is conduct at a temperature greater than about 25° C.

46. The method of claim 42 wherein said curing step is conduct at a temperature between about 25° C. and 70° C.

47. The method of claim 42 wherein said curing step is conduct at a temperature between about 40° C. and 70° C.

* * * * *